US005559011A

United States Patent [19]

Kapoor et al.

[11] Patent Number: 5,559,011
[45] Date of Patent: Sep. 24, 1996

[54] NUCLEIC ACIDS ENCODING MEMBRANE-ASSOCIATED IMMUNOGENS OF MYCOBACTERIAL AND CORRESPONDING PROBES, VECTORS, AND TRANSFORMED HOST CELLS

[76] Inventors: Archana Kapoor, Maison De L. Inde, 35 Boulvard Jourdan, 75014 Paris, France; Anil Munshi, 9450 Gilman Dr. No, 920573, LaJolla, Calif. 92092-0573

[21] Appl. No.: 192,632

[22] Filed: Feb. 7, 1994

Related U.S. Application Data

[62] Division of Ser. No. 906,395, Jun. 29, 1992, Pat. No. 5,330,754.

[51] Int. Cl.$^6$ .............................. C12N 15/31; C12N 1/21

[52] U.S. Cl. .................... 435/69.3; 536/23.7; 536/24.32; 435/320.1; 435/240.2; 435/252.3; 435/254.11

[58] Field of Search .............................. 536/23.57, 24.32; 435/320.1, 240.2, 252.3, 254.11, 69.3

[56] References Cited

PUBLICATIONS

Bloom, et al., *Science,* 257:1055–1063 (1992).

Rastogi, et al., *Clinical Infectious Diseases,* 14:308–312 (1992).

Fine, et al., *The Lancet,* Aug. 30, pp. 499–502 (1986).

La Vaccination Antitubercueuse, in "Rapport d'un Groupe Scientifique Organisation mondiale de la Sante", Série de Rapports Tech., 651 pp. 1–23 (1980).

Chaparas, et al., *American Review of Respiratory Disease,* 122:533–542 (1980).

Hopwood, et al., *British Medical Bulletin,* 44:528–546 (1988).

Bloom, *International Journal of Leprosy,* 58:365–375 (1990).

Kaufman, *Res. Microbiol.,* 141:765–768 (1990).

Falla, et al., *Infection and Immunity.* 59:2265–2273 (1991).

Bermudez, et al., *Infection and Immunity,* 59:1697–1702 (1991).

Havlir, et al., *Infection and Immunity,* 59:665–670 (1991).

Sussman, et al., *Infection and Immunity,* 59:2828–2835 (1991).

Blanchard, et al., *Infection and Immunity,* 59:2396–2402 (1991).

Denis, *Clin. exp. Immunol.,* 83:466–471 (1991).

Wadee, et al., *Infection and Immunity,* 57:864–86 9 (1989).

Pedrazzini, et al., *The Journal of Immunology,* 139:2032–2037 (1987).

Ramasesh, et al., *Infection and Immunity,* 59:2864–2869 (1991).

Praputpittaya, et al., *Clin. exp. Immunol.,* 70:298–306 (1987).

(List continued on next page.)

*Primary Examiner*—David L. Fitzgerald
*Attorney, Agent, or Firm*—Richard F. Trecartin; Flehr, Hohbach, Test, Albritton & Herbert

[57] ABSTRACT

Nucleic acid encoding four novel immunodeterminant protein antigens of *M. bovis* BCG, which is a vaccine strain for tuberculosis, have been isolated. These genes were isolated as immunoreactive recombinant clones from a genomic library of *M. bovis* BCG DNA, constructed in pBR322 vector, and screened with sera collected from tuberculosis patients. The BCG DNA insert of one of the recombinants, pMBB51A, which expressed an antigen of Mr 90 kD, was sequenced completely and an ORF encoding 761 amino acids encoding a protein of deduced molecular weight 79 kD, was identified. This gene was identified to encode a membrane bound, ion-motive ATPase of *M. bovis* BCG. The approach described here can be used to identify immunogens of mycobacteria. In addition, the well-characterized *M. bovis* BCG antigens can be used in the prevention, diagnosis and treatment of tuberculosis. The 79 kD antigen is also useful in the design of recombinant vaccines against different pathogens. The sequence of the 79 kD membrane-associated polypeptides also are useful for the development of specific PCR amplification based diagnostic procedures for the detection of mycobacteria. Also, the promoter of the 79 kD antigen is useful for expressing homologous and/or heterologous antigens in mycobacteria.

12 Claims, 11 Drawing Sheets

PUBLICATIONS

Bradley, *Journal of Bacteriology* 113:645–651 (1973).
Imaeda, et al., *International Journal of Systematic Bacteriology*, 32:456–458 (1982).
Imaeda, *International Journal of Systematic Bacteriology*, 35:147–150 (1985).
Clark–Curtiss, et al., *Journal of Bacteriology*, 161:1093–1102 (1985).
Garcia, et al., *Journal of General Microbiology*, 132:2265–2269 (1986).
Wasem, et al., *Journal of Clinical Microbiology*, 29:264–271 (1991).
Eisenach, et al., *Am Rev Respir Dis*, 133:1065–1068 (1986).
Minden, et al., *Infection and Immunity*, 46:519–525 (1984).
Closs, et al., *Scand. J. Immunol.*, 12:249–263 (1980).
Daniel, et al., *Microbiological Reviews*, 42:84–113 (1978).
Engers, et al., *Infect. Immun.*, 51:718–720 (1986).
Engers, et al., *Infect. Immun.*, 48:603–605 (1985).
Ljungqvist, et al., *Infection and Immunity*, 56:1994–1998 (1988).
Kadival, et al., *Journal of Clinical Microbiology*, 25:76–80 (1987).
Rouse, et al., *Infection and Immunity*, 58:1445–1449 (1990).
Worsaae, et al., *Journal of Clinical Microbiology*, 26:2608–2614 (1988).
Coates, et al., *The Lancet*, Jul. 25, pp. 167–169 (1981).
Young, et al., *Nature*, 316:450–452 (1985).
Young, et al., *Proc. Natl. Acad. Sci. USA*, 82:2583–2587 (1985).
Shinnick, et al., *Infection and Immunity*, 55:1932–1935 (1987).
Shinnick, et al., *Infection and Immunity*, 55:1718–1721 (1987).
Husson, et al., *Proc. Natl. Acad. Sci. USA*, 84:1679–1683 (1987).
Lu, et al., *Infection and Immunity*, 55:2378–2382 (1987).
Young, et al., *Proc. Natl. Acad. Sci. USA*, 80:1194–1198 (1983).
Matsuo, et al., *Journal of Bacteriology*, 170:3847–3854 (1988).
Yamaguchi, et al., *FEBS Letters*, 240:115–117 (1988).
Yamaguchi, et al., *Infection and Immunity*, 57:283–288 (1989).
Radford, et al., *Infection and Immunity*, 56:921–925 (1988).
Harboe, et al., *Infection and Immunity*, 52:293–302 (1986).
Minden, et al., *Infection and Immunity*, 53:560–564 (1986).
Thole et al., *Infection and Immunity*, 50:800–806 (1985).
Jackett, et al., *Journal of Clinical Microbiology*, 26:2313–2318 (1988).
Chandramuki, et al., *Journal of Clinical Microbiology*, 27:821–825 (1989).
Suzuki, et al., *FEMS Microbiology Letters*, 44:73–76 (1987).
Katoch et al., *Proceedings of Indo–UK Symposium*, pp. 262–269, (1986).
Medow, et al., *Zbl. Bakt. Hyg. A*, 266:359–369 (1987).
Sela, et al., *Journal of Bacteriology*, 171:70–73 (1989).
Ramakrishnan, *Proceedings of Indo–UK Symposium*, pp. 254–261, (1986).
Bhargava, et al., *Journal of Bacteriology*, 172:2930–2934 (1990).
Snider, et al., *Am Rev Respir Dis*. 130:1095–1099 (1984).
Jones, et al., *Am Rev Respir Dis*, 125:640–643 (1982).
Bolivar, et al., *Gene*, 2:95–113 (1977).
Sharp, et al., *Nucleic Acids Research*, 16:8207–8210 (1988).
Young, et al., *Molecular Microbiology*, 6:133–145 (1992).
Collins, et al., *FEMS Microbiology Letters*, 43:53–56 (1987).
Parra, et al., *Infection and Immunity*, 59:3411–3417 (1991).
Young, et al., *Infection and Immunity*, 55:1421–1425 (1987).
Andersen, et al., *Infection and Immunity*, 56:1344–1351 (1988).
Jacobs, et al., *Infection and Immunity*, 52:101–109 (1986).
Cohen, et al., *Journal of Clinical Microbiology*, 25:1176–1180 (1987).
Shinnick, et al., *Nucleic Acids Research*, 17:1254 (1989).
Verbon, et al., *Journal of Bacteriology*, 174:1352–1359 (1992).
Kingston, et al., *Infection and Immunity*, 55:3149–3154 (1987).
Ashbridge, et al., *Nucleic Acids Research*, 17:1249 (1989).
Lamb, et al., *Eur. J. Immunol.*, 18:973–976 (1988).
Borremans, et al., *Infection and Immunity*. 57:3123–3130 (1989).
De Wit, et al., *Nucleic Acids Research*, 18:3995 (1990).
Vismara, et al., *Infection and Immunity*, 58:245–251 (1990).
Rumschlag, et al., *Journal of Clinical Microbiology*, 28:591–595 (1990).
Thole, et al., *Infection and Immunity*, 58:80–87 (1990).
Andersen, et al., *Infection and Immunity*, 57:2481–2488 (1989).
Kadival, et al., *The Journal of Immunology*, 139:2447–2451 (1987).Praputpittaya, et al., *Clin. exp. Immunol.*, 70:307–315 (1987).
Young, et al., *Infection and Immunity*, 54:177–183 (1986).
Emmrich, et al., *J. Exp. Med.*, 163:1024–1029 (1986).
Mehra, et al., *Proc. Natl. Acad. Sci. USA*, 83:7013–7017 (1986).
Oftung, et al., *The Journal of Immunology*, 141:2749–2754 (1988).
Buchanan, et al., *Infection and Immunity*, 55:1000–1003 (1987).
Anderson, et al., *The Journal of Immunology*, 141:607–613 (1988).
Garsia, et al., *Infection and Immunity*, 57:204–212 (1989).
Britton, et al., *J. Exp. Med.*, 164:695–708 (1986).
Peake, et al., *The Journal of Biological Chemistry*, 266:20828–20832 (1991).
Davenport, et al., *Infection and Immunity*, 60:1170–1177 (1992).
Content, et al., *Infection and Immunity*, 59:3205–3212 (1991).
Abou–Zeid, et al., *Infection and Immunity*, 59:2712–2718 (1991).
Wiker, et al., *Infection and Immunity*, 58:272–274 (1990).
Davis, et al., *Journal of Bacteriology*, 173:5653–5662 (1991).
Suzuki, et al., *Journal of Bacteriology*, 170:2886–2889 (1988).
Young, et al., *Infection and Immunity*, 59:3086–3093 (1991).
Lathigra, et al., *Nucleic Acids Research*, 16:1636 (1988).
Baird, et al., *Nucleic Acids Research*, 16:9047 (1988).
Patel, et al., *Journal of Bacteriology*, 173:7982–7987 (1991).
Nerland, et al., *Journal of Bacteriology*, 170:5919–5921 (1988).
Flaherty, et al., *Nature*, 346:623–628 (1990).
Young, et al., *Proc. Natl. Acad. Sci. USA*, 85:4267–4270 (1988).

Nagai, et al., *Infection and Immunity*, 59:372–382 (1991).
Andersen, et al., *Infection and Immunity*, 59:1905–1910 (1991).
Fifis, et al., *Infection and Immunity*, 59:800–807 (1991).
Worsaee, et al., *Infection and Immunity*, 55:2922–2927 (1987).
Abou–Zeid, et al., *Infection and Immunity*, 56:3046–3051 (1988).
Abou–Zeid, et al., *Journal of General Microbiology*, 134:531–538 (1988).
Abou–Zeid, et al., *Infection and Immunity*, 55:3213–3214 (1987).
Thole, et al., *Molecular Microbiology*, 6:153–163 (1992).
Chatterjee, et al., *Infection and Immunity*, 57:322–330 (1989).
Chan, et al., *Infection and Immunity*, 59:1755–1761 (1991).
Belisle, et al., *Journal of Bacteriology*, 173:6991–6997 (1991).
Larsson, et al., *Journal of Clinical Microbiology*, 27:2388–2390 (1989).
Larsson, et al., *Journal of Clinical Microbiology*, 27:2230–2233 (1989).
Katila, et al., *Journal of Clinical Microbiology*, 29:355–358 (1991).
Wheeler, et al., *Infection and Immunity*, 59:3781–3789 (1991).
Rouse, et al., *Infection and Immunity*, 59:2595–2600 (1991).
Belisle, et al., *Journal of Bacteriology*, 173:6991–6997 (1991).
Choubey, et al., *Current Microbiology*, 13:171–175 (1986).
Amicosante, et al., *Biochem. J.*, 271:729–734 (1990).
Morris, et al., *Infection and Immunity*, 56:3026–3031 (1988).
Kieser, et al., *Journal of Bacteriology*, 168:72–80 (1986).
Lamb, *Proceedings of Indo–UK Symposium*, pp. 288–297, (1986).
Jacobs, et al., *Proc. Natl. Acad. Sci., USA*, 83:1926–1930 (1986).
Lamb, et al., *The Journal of Immunology*, 144:1922–1925 (1990).
Cherayil, et al., *The Journal of Immunology*, 141:4370–4375 (1988).
Sela, et al., *Infection and Immunity*, 59:4117–4124 (1991).
Thangaraj, et al., *Infection and Immunity*, 58:1937–1942 (1990).
Houssaini–Iraqui, et al., *FEMS Microbiology Letters*, 90:239–244 (1992).
Nath, et al., *Nucleic Acids Research*, 18:4935 (1990).
Shoemaker, et al., *Am Rev Respir Dis*, 134:210–213 (1986).
Wards, et al., *Journal of Clinical Microbiology*, 25:2309–2313 (1987).
Patel, et al., *Journal of General Microbiology*, 132:541–551 (1986).
Otal, et al., *Journal of Clinical Microbiology*, 29:1252–124 (1991).
Collins, et al., *Journal of General Microbiology*, 130:1019–1021 (1984).
Levy–Frebault, et al., *Journal of Clinical Microbiology*, 27:2823–2826 (1989).
Zainuddin, et al., *Journal of General Microbiology*, 135:2347–2355 (1989).
Whipple, et al., *Veterinary Microbiology*, 19:189–194 (1989).
Whipple, et al., *Journal of Clinical Microbiology*, 25:1511–1515 (1987).
Clark–Curtiss, et al., *Journal of Bacteriology*, 171:4844–4851 (1989).
Clark–Curtiss, et al., *The Journal of Infectious Diseases*, 159: 7–15 (1989).
Reddi, et al., *International Journal of Leprosy*, 56:592–598 (1988).
Eisenach, et al., *Journal of Clinical Microbiology*, 26:2240–2245 (1988).
Musial, et al., *Journal of Clinical Microbiology*, 26:2120–2123 (1988).
Drake, et al., *Journal of Clinical Microbiology*, 25:1442–1445 (1987).
Saito, et al., *Journal of Clinical Microbiology*, 27:994–997 (1989).
Stager, et al., *Journal of Clinical Microbiology*, 29:154–157 (1991).
Thoresen, et al., *Journal of Clinical Microbiology*, 29:625–626 (1991).
Kiehn, et al., *Journal of Clinical Microbiology*, 25:1551–1552 (1987).
Pao, et al., *Tubercle*, 69:27–36 (1988).
Sada, et al., *Journal of Clinical Microbiology*, 28:2587–2590 (1990).
Wadee, et al., *Journal of Clinical Microbiology*, 28:2786–2791 (1990).
Patel, et al., *Reviews of Infectious Diseases*, 11:5411–5419 (1989).
Papa, et al., *Res. Microbiol.*, 143:327–331 (1992).
Papa, et al., *Journal of Clinical Microbiology*, 25:2270–2273 (1987).
Shoemaker, et al., *Am Rev Respir Dis*, 131:760–763 (1985).
Vadiee, et al., *Clin. ex. Immunol.*, 79:397–402 (1990).
Patil, et al., *Journal of Clinical Microbiology*, 28:2792–2796 (1990).
Levis, et al., *Journal of Clinical Microbiology*, 24:917–921 (1986).
Sritharan, et al., *Molecular and Cellular Probes*, 5:385–395 (1991).
Patel, et al., *Journal of Clinical Microbiology*, 28:513–518 (1990).
Sjobring, et al., *Journal of Clinical Microbiology*, 28:2200–2204 (1990).
De Wit, et al., *Journal of Clinical Microbiology*, 28:2437–2441 (1990).
Plikaytis, et al., *Journal of Clinical Microbiology*, 28:1913–1917 (1990).
Hance, et al., *Molecular Microbiology*, 3:843–849 (1989).
Brisson–Noel, et al., *The Lancet*, Nov. 4, pp. 1069–1071 (1989).
Hartskeerl, et al., *Journal of General Microbiology* 135:2357–2364 (1989).
Pierre, et al., *Journal of Clinical Microbiology*, 29:712–717 (1991).
Brisson-Noel, et al., *The Lancet*, 338:364–366 (1991).
Martin, et al., *Nature*, 345:739–743 (1990).
Martin, et al., in *"Molecular Biology of the Mycobacteria"*, Surrey University Press, pp. 121–137 (1990).
Thierry, et al., *Nucleic Acids Research*, 18:188 (1990).
Guilhot, et al., *Molecular Microbiology*, 6:107–113 (1992).
McAdam, et al., *Molecular Microbiology*, 4:1607–1613 (1990).
Cirillo, et al., *Journal of Bacteriology*, 173:7772–7789 (1991).
Hermans, et al., *Infection and Immunity*, 59:2695–2705 (1991).

Thierry, et al., *Journal of Clinical Microbiology*, 28:000–000 (1990).
Husson, et al., *Journal of Bacteriology*, 172:519–524 (1990).
Martin, et al., *Molecular Microbiology*, 5:2499–2502 (1991).
Snapper, et al., *Proc. Natl. Acad. Sci. USA*, 85:6987–6991 (1988).
Lee, et al., *Proc. Natl. Acad. Sci. USA*, 88:3111–3115 (1991).
Kalpana, et al., *Proc. Natl. Acad. Sci. USA*, 88:5433–5437 (1991).
Hinshelwood, et al., *Gene*, 110:115–118 (1992).
Radford, et al., *Plasmid*, 25:149–153 (1991).
Ranes, et al., *Journal of Bacteriology*, 172:2793–2797 (1990).
Rauzier, et al., *Gene*, 71:315–321 (1988).
Lazraq, et al., *FEMS Microbiology Letters*, 69:135–138 (1990).
Jacobs, et al., *Nature*, 327:532–535 (1987).
Gopinathan, et al., *Proceedings of Indo–UK Symposium*, pp. 270–287, (1986).
Hermans, et al., *Molecular Microbiology*, 5:1561–1566 (1991).
Lazraq, et al., *Current Microbiology*, 22:9–13 (1991).
Bartow, et al., *Infection and Immunity*, 57:1374–1379 (1989).
Hubbard, et al., *Infection and Immunity*, 59:2012–2016 (1991).
Haslov, et al., *Scand. J. Immunol.*, 29:281–288 (1989).
Lamb, et al., *The EMBO Journal*, 6:1245–1249 (1987).
Boom, et al., *Infection and Immunity*, 55:2223–2229 (1987).
Mustafa, et al., *Journal of Immunology*, 141:2729–2733 (1988).
Lamb, et al., *Immunology*, 60:1–5 (1987).
Oftung, et al., *The Journal of Immunology*, 138:927–931 (1987).
Leveton, et al., *Infection and Immunity*, 57:390–395 (1989).
Dockrell, et al., *Infection and Immunity*, 57:1979–1983 (1989).
Laal, et al., *Proc. Natl. Acad. Sci. USA*, 88:1054–1058 (1991).
Janson, et al., *The Journal of Immunology*, 147:3430–3537 (1991).
Sathish, et al., *Infection and Immunity*, 58:1327–1336 (1990).
Cristina, et al., *Journal of Clinical Microbiology*, 27:2184–2189 (1989).
Rumschlag, et al., *Journal of Clinical Microbiology*, 26:2200–2202 (1988).
Vega-Lopez, et al., *Journal of Clinical Microbiology*, 26:2474–2479 (1988).
Doherty, et al., *The Journal of Immunology*, 146:1934–1940 (1991).
Gillis, et al., *Infection and Immunity*, 49:371–377 (1985).
Mandock, et al., *Zbl. Bakt. Hyg. A*, 265:12–19 (1987).
Steward, et al., *Immunology Today*, 8:51–58 (1987).
Convit, et al., *The Lancet*, 339:446–450 (1992).
Charles, et al., *TIBTECH*, 8:117–120 (1990).
Curtiss III, et al., *Res. Microbiol.*, 141:797–805 (1990).
Aldovini, et al., *Nature*, 351:479–482 (1991).
Barletta, et al., *Res. Microbio.*, 141:931–939 (1990).
Desrosiers, *Current Biology*, 2:162–163 (1992).
Stover, et al., *Nature*, 351:456–460 (1991).
Winter, et al., *Gene*, 109:47–54 (1991).

Matsuo, et al., *Infection and Immunity*, 58:4049–4054 (1990).
Leclerc, et al., *The Journal of Immunology*, 147:3545–3552 (1991).
Schlienger, et al., *Journal of Virology*, 66:2570–2576 (1992).
Charbit, et al., *Aids*, 4:545–551 (1990).
van der Werf, et al., *Vaccine*, 8:269–277 (1990).
Meylan, et al., *The Journal of Infectious Diseases*, 165:80–86 (1992).
Onorato, et al., *The Journal of Infectious Diseases*, 165:87–92 (1992).
Kiehn, et al., *Journal of Clinical Microbiology*, 21:168–173 (1985).
Wong, et al., *The American Journal of Medicine*, 78:35–40 (1985).
Haseltine, *The FASEB Journal*, 5:2349–2360 (1991).
Riviere, et al. *Journal of Virology*, 63:2270–2277 (1989).
Javaherian, et al., *Proc. Natl. Acad. Sci. USA*, 86:6768–6772 (1989).
Roof, et al., *Journal of Bacteriology*, 173:5554–5557 (1991).
Michaelis, et al., *Journal of Bacteriology*, 154:356–365 (1983).
Boyd, et al., *Proc. Natl. Acad. Sci. USA*, 84:8525–8529 (1987).
Newton, et al., *Molecular Microbiology*, 5:2511–2518 (1991).
Manoil, et al., *Proc. Natl. Acad. Sci. USA*, 82:8129–8133 (1985).
Charbit, et al., *Journal of Bacteriology*, 173:262–27 5 (1991).
Ehrmann et al., *Proc. Natl. Acad. Sci. USA*, 87:7574–7578 (1990).
Manoil, et al., *Journal of Bacteriology*, 172:515–518 (1990).
Hoffman, et al., *Proc. Natl. Acad. Sci. USA*, 82:5107–5111 (1985).
Manoil, *Journal of Bacteriology*, 172:1035–1042 (1990).
Rosen, In "Escherichia coli and Salmonella typhimurium" F. C. Neidhardt (Ed.), *Am. Soc. Microbiol.* (Publ.) Washington, D.C., pp. 760–767 (1987).
Maloney, In "Escherichia coli and Salmonella typhimurium" F. C. Neidhardt (Ed.), *Am. Soc. Microbiol.* (Publ.), Washington, D.C., pp. 222–243 (1987).
Furst, et al., *J. Biol. Chem.*, 260:50–52 (1985).
Kakinuma, et al., *The Journal of Biological Chemistry*, 260:2086–2091 (1985).
Kakinuma, *Journal of Bacteriology*, 169:3886–3890 (1987).
Furst, et al., *The Journal of Biological Chemistry*, 261:4302–4308 (1986).
Hugentobler, et al., *The Journal of Biological Chemistry*, 258:7611–7617 (1983).
Schlosser, et al., *Journal of Bacteriology*, 173:3170–3176 (1991).
Solioz, et al., *The Journal of Biological Chemistry*, 262:7358–7362 (1987).
Waser, et al., *The Journal of Biological Chemistry*, 267:5396–5400 (1992).
Angov, et al., *Journal of Bacteriology*, 173:407–411 (1991).
Walderhaug, et al., *Journal of Bacteriology*, 171:1192–1195 (1989).
Epstein, et al., *TIBS*, Jan., pp. 21–23 (1980).
Laimins, et al., *Proc. Natl. Acad. Sci. USA*, 75:3216–3219 (1978).

Dosch, et al., *Journal of Bacteriology*, 173:687–696 (1991).
Epstein, et al., *The Journal of Biological Chemistry*, 253:6666–6668 (1978).
Pedersen, et al., *TIBS*, 12:146–149 (1987).
Hesse, et al., *Biochemistry*, 81:4746–4750 (1984).
Ghislain, et al., *The Journal of Biological Chemistry*, 265:18400–18407 (1990).
Foury, *The Journal of Biological Chemistry*, 265:18554–18560 (1990).
Kawakami, et al., *J. Biochem.*, 100:389–397 (1986).
Karlish, et al., *Proc. Natl. Acad. Aci. USA*, 87:4566–4570 (1990).
Kawakami, et al., *Nature*, 316:733–736 (1985).
Martin–Vasallo, et al., *Journal of Biological Chemistry*, 264:4613–4618 (1989).
Schneider, et al., *Blood Cells*, 13:299–307 (1987).
Gallice, et al., *Clin. Chem.*, 34:2044–2047 (1988).
Rayson, *The Journal of Biological Chemistry*, 263:11056–11058 (1988).
Ovchinnikov, et al., *FEBS Letters*, 201:237–245 (1986).
Bender, et al., *Infection and Immunity*, 53:331–338 (1986).
Shull, et al., *Nature*, 316:691–695 (1985).
Hager, et al., *Proc. Natl. Acad. Sci. USA*, 83:76 93–7697 (1986).
Addison, *The Journal of Biological Chemistry*, 261:14896–14901 (1986).
Masugi, et al., *Clin. and Exper. Theory and Practice*, 9:1233–1242 (1987).
Kawai, et al., *Cancer Letters*, 35:147–152 (1987).
Umeda, et al., *Clin. and Exper.–Theory and Practice*, 9:1209–1219 (1987).
Crabos, et al., *American Physiological Society*, 254:F912–F917 (1988).
Harper, et al., *Proc. Natl. Acad. Sci. USA*, 86:1234–1238 (1989).
Monk, et al., *Journal of Bacteriology*, 173:6826:6836 (1991).
Scarborough, *Proc. Natl. Acad. Sci. USA*, 83:3688–3692 (1986).
Epstein, et al., *Current Topics in Membranes and Transport*, 23:153–175 (1985).
Isacoff, et al., *Nature*, 345:530–534 (1990).
Walderhaug, et al., in "Ion Transport in Prokaryotes", *Academic Press, Inc.*, pp. 85–130, (1987).
Farley, et al., *The Journal of Biological Chemistry*, 260:3899–3901 (1985).
Brandl, et al., *Proc. Natl. Acad. Sci. USA*, 83:917–921 (1986).
Ohta, et al., *Proc. Natl. Acad. Sci. USA*, 83:2071–2075 (1986).
Rao, et al., *Biochemia et Biophysica Acta*, 869:197–214 (1986).

|— 1kb —|
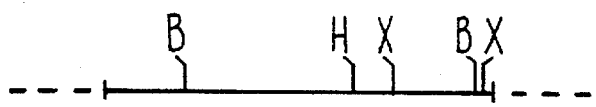 Y3275 (12kDa)
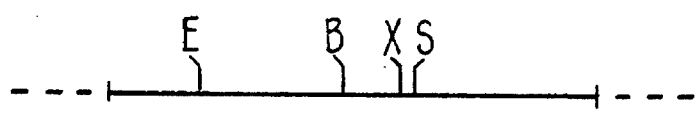 Y3145 (14kDa)
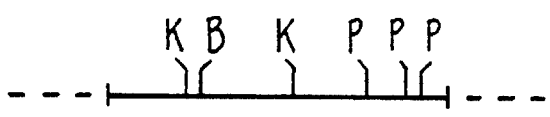 Y3147 (19kDa)
 Y3143 (65kDa)
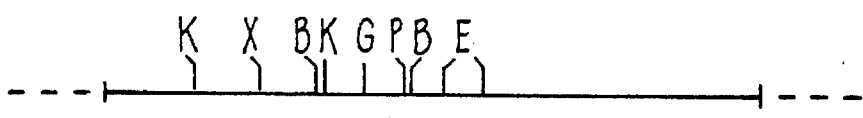 Y3271 (71kDa)
Fig. 2A

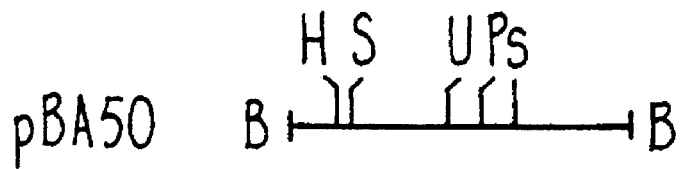
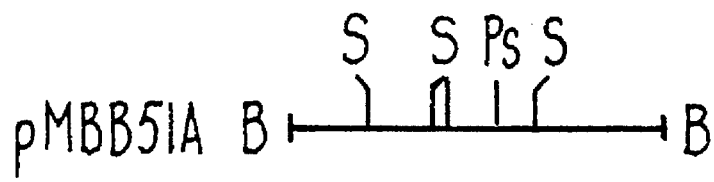
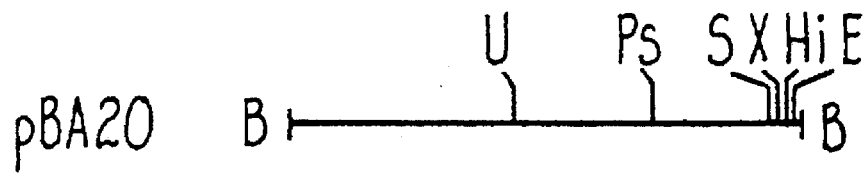
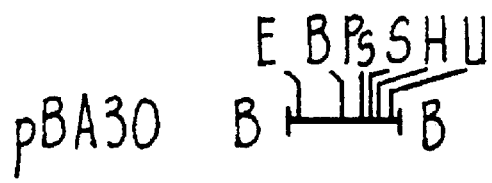
Fig. 2B

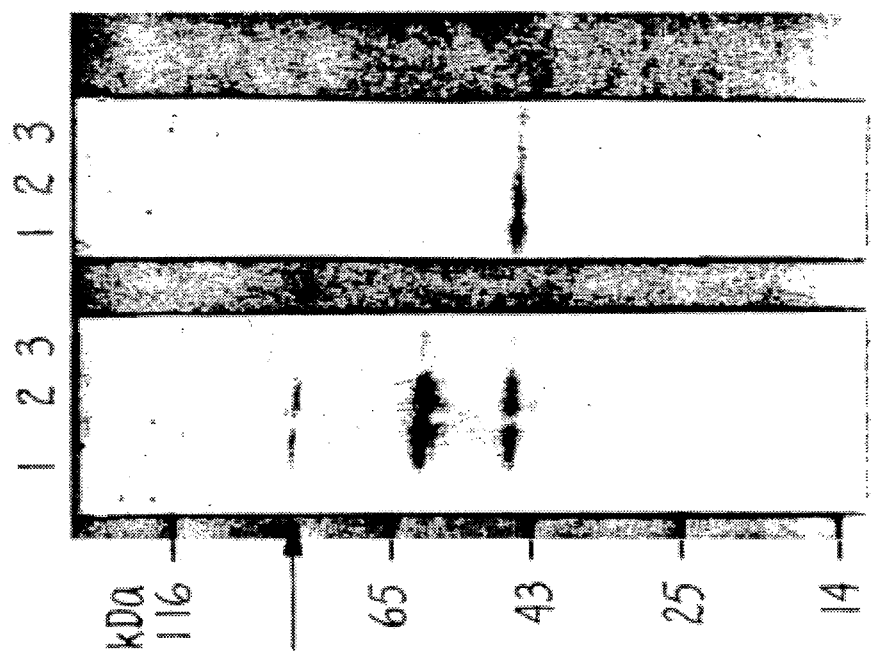
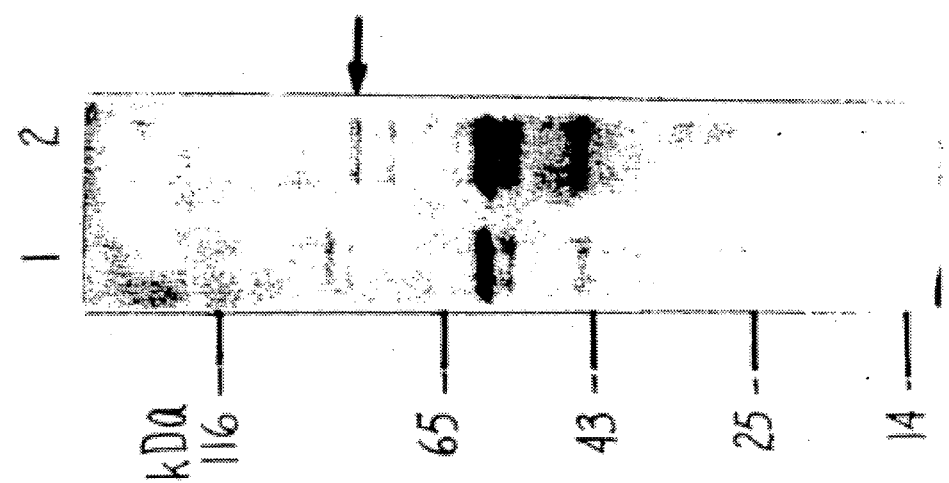

Fig. 4A

```
GGATCCCGCGGTCATCGATCGGGTCAAACACCGCCTCGACGGTTCACGCTGCGCCGCGGGAGGTG
GTGGCCGGCAGCCACGCATCTACTACGGCACCATCCTGACCGTGACCCTTCACTGCGAGCGCAACCGG
CTGCACCACGAACTCGGGCGCTATGGCCCTCGAAATGGAAGGCGGTGCGCGGTGCAAATCTGCGCGTCCTTCGATATCCC
ATGGCTGGTCATTCGCGCGCTCTCCGATCTCGCCGGACCCGATTCGGGGGTGGACTTCAATCGGTTTGTCGGCGAGGTGG
                                                                        80

-35              -10           480
CGGCCAGTTCGGCCCGCGGTTCGCTGCGCCGGTGTTGACGGCCTGTTGAAGACGACTATCCGCCGGTTC

ACCGCGTCAGGCGGCTTCGGTGAGGTGAGTAATTTGGTCATTAACTTGGTCATGCCGCCGATGTTGAGCGGAGGCCA
                 S/D  508
CAGGTCGGCCCGGAAGTGAGGAGCCACG ATG ACG GCC GCC GTG ACC GGT GAA CAC CAC GCG AGT GTG
                             MET Thr Ala Ala Val Thr Gly Glu His His Ala Ser Val
                              1                                                600
CAG CGG ATA CAA CTC AGA ATC AGC GGG ATG TCG TCT GCG TGC CGT GTG GAA
Gln Arg Ile Gln Leu Arg Ile Ser Gly MET Ser Cys Ala Cys Arg Val Glu
              550                                                       650
TCG ACC CTC AAC AAG CTG CCG GGG GTT CGG GCA GCT GTG AAC TTC GGC ACC CGG GTG GCA
Ser Thr Leu Asn Lys Leu Pro Gly Val Arg Ala Ala Val Asn Phe Gly Thr Arg Val Ala

ACC ATC GAC ACC AGC GAG GCG GTC GAC GCT GCC GCG CTG TGC CAG GCG GTC CGC CGC GCG
Thr Ile Asp Thr Ser Glu Ala Val Asp Ala Ala Ala Leu Cys Gln Ala Val Arg Arg Ala
                                                              700
GGC TAT CAG GCC GAT CTG TGC ACG GAT GAC GGT CGG AGC GCG AGT GAT CCG GAC GCC GAC
Gly Tyr Gln Ala Asp Leu Cys Thr Asp Asp Gly Arg Ser Ala Ser Asp Pro Asp Ala Asp
                                      750
CAC GCT CGA CAG CTG CTG ATC CGG CTA GCG ATC GCC ATC GCC GTG CTG TTT GTG CCC GTG GCC
His Ala Arg Gln Leu Leu Ile Arg Leu Ala Ile Ala Ala Val Leu Phe Val Pro Val Ala
                 800
```

Fig. 4B

```
850                                              900
GAT CTG TCG GTG ATG TTT GGG GTC GTG CCT GCC ACG CGC TTC ACC GGC TGG CAG TGG GTG
Asp Leu Ser Val MET Phe Gly Val Val Pro Ala Thr Arg Phe Thr Gly Trp Gln Trp Val
                    120                                            950
CTA AGC GCG CTG GCA CTG GCC CTG GTC GTG GTG ACC TGG GCG GCG TGG CCG TTT CAC CGC GTT GCG
Leu Ser Ala Leu Ala Leu Pro Val Val Thr Trp Ala Ala Trp Pro Phe His Arg Val Ala
                    140                                     1000
ATG CGC AAC GCC CGC CAC CAC GCC GCC TCC ATG GAG ACG CTA ATC TCG GTC GGT ATC ACG
MET Arg Asn Ala Arg His His Ala Ser MET Glu Thr Leu Ile Ser Val Gly Ile Thr
                    160                  1050
GCC GCC ACG ATC TGG CTG TAC ACC GTC TTC GGC AAT CAC TCG CCC ATC GAG CGC AGC
Ala Ala Thr Ile Trp Leu Tyr Thr Val Phe Gly Asn His Ser Pro Ile Glu Arg Ser
                    180      1100
GGC ATA TGG CAG GCG CTG CTG GGA AGC GAT GCT ATT TAT TTC GAG GCG GCG GGT GTC
Gly Ile Trp Gln Ala Leu Leu Gly Ser Asp Ala Ile Tyr Phe Glu Ala Ala Gly Val
                    200                                 1200
ACG GTG TTC GTG CTG GTG GGG TAT TTC GAG CGC GCC AAG TCG CAG GCG AGT
Thr Val Phe Val Leu Val Gly Arg Tyr Phe Glu Arg Ala Lys Ser Gln Ala Gly Ser
1150                220                                       1250
GCG CTG AGA GCC TTG GCG CTG AGC GCC AAG GAA GTA GCC GTC CTG CTA CCG GAT GGG
Ala Leu Arg Ala Leu Ala Leu Ser Ala Lys Glu Val Ala Val Leu Leu Pro Asp Gly
                    240
TCG GAG ATG GTC ATC CCG GAC GAA CTC AAA GAA CAG CAG CGC TTC GTG GTG CGT CCA
Ser Glu MET Val Ile Pro Asp Glu Leu Lys Glu Gln Gln Arg Phe Val Val Arg Pro
                    260     1300
GGG CAG ATA GTT GCC GCC GAC GGC CTC GCC GTC GAC GGG TCC GCT GCG GTC GAC ATG AGC
Gly Gln Ile Val Ala Ala Asp Gly Leu Ala Val Asp Gly Ser Ala Ala Val Asp MET Ser
                    280   1350
```

```
GCG ATG ACC GGC GAG GCC AAA CCG ACC CGG GTG CGT CCG GGG GGG CAG GTC ATC GGC GGC
Ala MET Thr Gly Glu Ala Lys Pro Thr Arg Val Arg Pro Gly Gly Gln Val Ile Gly Gly
                         300                                    1500
ACC ACA GTG CTT GAC GGC CGG CTG ATC GTG GAG GCG GTG GCC GCC GAC ACC CAG
Thr Thr Val Leu Asp Gly Arg Leu Ile Val Glu Ala Val Ala Ala Asp Thr Gln
 1450                    320
TTC GCC GGA ATG GTC CGC CTC CGT GTT GAG CAA GCA CAG GCG CAA AAG GAC GCA CAG CGA
Phe Ala Gly MET Val Arg Leu Arg Val Glu Gln Ala Gln Ala Gln Lys Asp Ala Gln Arg
                        340             1550
CTA GCC GAC CGG ATC TCC GTG GCT CCC GCT GTG TTG GTT ATC CTA ACC
Leu Ala Asp Arg Ile Ser Val Ala Pro Ala Val Leu Val Ile Leu Thr
                        360         1600
GCA GCC GGA TGG CTA ATC GCC GGG GGA CAA CCC GAC CGT GCC TCG GCC CTC GCC
Ala Ala Gly Trp Leu Ile Ala Gly Gly Gln Pro Asp Arg Ala Ser Ala Leu Ala
                        380     1650
GTG CTT GTC ATC GCC CCG TGT CTG GGG CTG GCC ACT CCG ACC GCG ATG ATG GTG
Val Leu Val Ile Ala Pro Cys Leu Gly Leu Ala Thr Pro Thr Ala MET MET Val
 1700                   400                                    1800
GCC TCT GGT CGC GGT GCC CAG CTC GGA ATA TTT CTG AAG GGC TAC AAA TCG GAG GCC
Ala Ser Gly Arg Gly Ala Gln Leu Gly Ile Phe Leu Lys Gly Tyr Lys Ser Glu Ala
 1750                   420
ACC CGC GCG GTG GAC ACC GTC TTC GAC AAG ACC GGC ACC CTG ACG ACG CGG CTG
Thr Arg Ala Val Asp Thr Val Phe Asp Lys Thr Gly Thr Leu Thr Thr Arg Leu
                        440     1850
CAG GTC AGT GCC GTG ACC GTG ACG GCA CCG GCG GAG TGG GGC GAC CAG GTG CTC GCC TTG GCC
Gln Val Ser Ala Val Thr Val Thr Ala Pro Ala Glu Trp Gly Asp Gln Val Leu Ala Leu Ala
                        460                     1900
```

```
GCG ACC GTG GAA GCC GCG TCC GAG CAC TCG GTG GCG CTC GCG ATC GCC GCG GCA ACG ACT
Ala Thr Val Glu Ala Ala Ser Glu His Ser Val Ala Leu Ala Ile Ala Ala Ala Thr Thr
                        480       1950                                            
CGG CGA GAC GCG GTC ACC GAC TTT CGC GCC ATA CCC GGC GTC CGC AGC GGC GTC ACC GTG
Arg Arg Asp Ala Val Thr Asp Phe Arg Ala Ile Pro Gly Val Arg Ser Gly Val Thr Val
            2000               500                                                
TCC GGG CGG GCG GTA CGG GTG GGC AAA CCG TCA TGG ATC GGG TCC TCG TGC CAC CCC
Ser Gly Arg Ala Val Arg Val Gly Lys Pro Ser Trp Ile Gly Ser Ser Cys His Pro
 2050                       520                                       2100
AAC ATG CGC GCC GCG CGG CGC CAC GCC GAA TCG CTG GGT GAG ACG GCC GTA TTC GTC GAG
Asn MET Arg Ala Ala Arg Arg His Ala Glu Ser Leu Gly Glu Thr Ala Val Phe Val Glu
                    540                                   2150
GTC GAC GGC GAA CCA TGC GGC GTC ATC GCG GCC GAC GTC AAG GAC TCG GCG CGA
Val Asp Gly Glu Pro Cys Gly Val Ile Ala Ala Asp Val Lys Asp Ser Ala Arg
                560                        2200
GAC GCC GTG GCC GCC CTG GCC GAT CGT GGT CTG CGC ACC ATG CTG TTG ACC GGT GAC AAT
Asp Ala Val Ala Ala Leu Ala Asp Arg Gly Leu Arg Thr MET Leu Leu Thr Gly Asp Asn
                    580                              2250
CCC GAA TCG GCG GCG GCT ACT CGC GTG GCT ATC GAG CAG CTA CGC GAC CGC GAC ATC GCC
Pro Glu Ser Ala Ala Ala Thr Arg Val Ala Ile Glu Gln Leu Arg Asp Arg Ile Ala
                600                  2300                                   2400
CTG CCG GAA GGC AAG GTC GAT GTC ATC GAG GTG CAT GTC GTC GCC
Leu Pro Glu Gly Lys Val Asp Val Ile Glu Val His Val Val Ala
2350                620
ATG GTC GGT GAC GGC ATC AAC GAC GGA CCC GCA CTG GCC CGT GCC GAT CTA GGA ATG GCC
MET Val Gly Asp Gly Ile Asn Asp Gly Pro Ala Leu Ala Arg Asp Leu Gly MET Ala
                    640                       2450
```

```
ATC GGG CGC GGC ACG GAC GTC GCG ATC GGT GCC GAC ATC ATC TTG GTC CGC GAC CAC
Ile Gly Arg Gly Thr Asp Val Ala Ile Gly Ala Ala Asp Ile Ile Leu Val Arg Asp His
                                    660                               2500

CTC GAC GTT GTA CCC CTT GCG CTT GAC CTG GCA AGG GCC ACG ATG CGC ACC GTC AAA CTC
Leu Asp Val Val Pro Leu Ala Leu Asp Leu Ala Arg Ala Thr MET Arg Thr Val Lys Leu
                      2550                          680

AAC ATG GTC TGG GCA TTC GGA TAC AAC ATC GCC GCG ATT CCC GTC GCC GCT GCC GGA CTG
Asn MET Val Trp Ala Phe Gly Tyr Asn Ile Ala Ala Ile Pro Val Ala Ala Ala Gly Leu
           2600                     700

CTC AAC CCC CTG GTC GCC GGT GCG GCC ATG GCG TTC TCA TCG TTC TTC GTG GTC TCA AAC
Leu Asn Pro Leu Val Ala Gly Ala Ala MET Ala Phe Ser Ser Phe Phe Val Val Ser Asn
  2650                              720                                  2700

AGC TTG CGG TTG CGC AAA TTT GGG CGA TAC CCG CTA GGC TGC GGA ACC GTC GGT GGG CCA
Ser Leu Arg Leu Arg Lys Phe Gly Arg Tyr Pro Leu Gly Cys Gly Thr Val Gly Gly Pro
                                    740         2750

CAA ATG ACC GCG CCG TCG TCC GCG TGA TGCGTTGTCGGGCAACACGATATCGGGCTCAGCGGGACCGCA
Gln MET Thr Ala Pro Ser Ser Ala TER
                            761

TCCGGTCTCGCGCCGAGGACCAGAGGCGCTTCGCCACCATGATTGCCAGGACCGGCCGATCACCACCGGCAGATGAGT
CAAAATCCGGCGTGGTGCTGACCGCCGACCAGCCGATCCACAATCACATAGCCGGTCAGTATGGCGACGAACGCCGTCA
GAACACCGGCCAGGCGCGGCTCGCGCCACCCTCCATAGCGCCATGATCACCGAGCGCAATCGACCACGAC
GTGACTCGTTGAGCAAGTGGGCGCCGATCTCAGGGCCGACGTCTAGCCAACGTCCAAACCCCTGCACG
GTGCCCAGGGCGATCTGCCGATGCCCACGACCAACGCCCAAGTCGCCAGGTCATCGGTGAATGTTGCCGCCGCGG
CGCCCGGGATCC
 3250
```

Fig.4E

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
( A ) LENGTH: 3250 base pairs
( B ) TYPE: nucleic acid
( C ) STRANDEDNESS: single
( D ) TOPOLOGY: linear ( i i ) MOLECULE TYPE: DNA (genomic)

( i x ) FEATURE:
( A ) NAME/KEY: CDS
( B ) LOCATION: 508..2790

( x i ) SEQUENCE DESCRIPTION: SEQ ID NO:1:

```
GGATCCCGCG GTCATCGATC GGGTCAAACA CCGCCTCGAC GGGTTCACGC TGGCGCCGCT      60

GTCCACCGCC GCGGGAGGTG GTGGCCGGCA GCCACGCATC TACTACGGCA CCATCCTGAC     120

CGGTGACCAA TACCTTCACT GCGAGCGCAC CCGCAACCGG CTGCACCACG AACTCGGCGG     180

TATGGCCGTC GAAATGGAAG GCGGTGCGGT GGCGCAAATC TGCGCGTCCT TCGATATCCC     240

ATGGCTGGTC ATTCGCGCGC TCTCCGATCT CGCCGGAGCC GATTCGGGGG TGGACTTCAA     300

TCGGTTTGTC GGCGAGGTGG CGGCCAGTTC GGCCCGCGTT CTGCTGCGCT TGCTGCCGGT     360

GTTGACGGCC TGTTGAAGAC GACTATCCGC CGGTGCGTTC ACCGCGTCAG GCGGCTTCGG     420

TGAGGTGAGT AATTTGGTCA TTAACTTGGT CATGCCGCCG CCGATGTTGA GCGGAGGCCA     480

CAGGTCGGCC GGAAGTGAGG AGCCACG ATG ACG GCG GCC GTG ACC GGT GAA         531
                              Met Thr Ala Ala Val Thr Gly Glu
                               1               5

CAC CAC GCG AGT GTG CAG CGG ATA CAA CTC AGA ATC AGC GGG ATG TCG       579
His His Ala Ser Val Gln Arg Ile Gln Leu Arg Ile Ser Gly Met Ser
     10                  15                  20

TGC TCT GCG TGC GCC CAC CGT GTG GAA TCG ACC CTC AAC AAG CTG CCG       627
Cys Ser Ala Cys Ala His Arg Val Glu Ser Thr Leu Asn Lys Leu Pro
 25                  30                  35                  40

GGG GTT CGG GCA GCT GTG AAC TTC GGC ACC CGG GTG GCA ACC ATC GAC       675
Gly Val Arg Ala Ala Val Asn Phe Gly Thr Arg Val Ala Thr Ile Asp
                 45                  50                  55

ACC AGC GAG GCG GTC GAC GCT GCC GCG CTG TGC CAG GCG GTC CGC CGC       723
Thr Ser Glu Ala Val Asp Ala Ala Ala Leu Cys Gln Ala Val Arg Arg
             60                  65                  70
```

| | | | | | | | | | | | | | | | | |
|---|---|---|---|---|---|---|---|---|---|---|---|---|---|---|---|---|
| GCG | GGC | TAT | CAG | GCC | GAT | CTG | TGC | ACG | GAT | GAC | GGT | CGG | AGC | GCG | AGT | 771 |
| Ala | Gly | Tyr 75 | Gln | Ala | Asp | Leu | Cys 80 | Thr | Asp | Asp | Gly | Arg 85 | Ser | Ala | Ser | |
| GAT | CCG | GAC | GCC | GAC | CAC | GCT | CGA | CAG | CTG | CTG | ATC | CGG | CTA | GCG | ATC | 819 |
| Asp | Pro 90 | Asp | Ala | Asp | His | Ala 95 | Arg | Gln | Leu | Leu | Ile 100 | Arg | Leu | Ala | Ile | |
| GCC | GCC | GTG | CTG | TTT | GTG | CCC | GTG | GCC | GAT | CTG | TCG | GTG | ATG | TTT | GGG | 867 |
| Ala 105 | Ala | Val | Leu | Phe | Val 110 | Pro | Val | Ala | Asp | Leu 115 | Ser | Val | Met | Phe | Gly 120 | |
| GTC | GTG | CCT | GCC | ACG | CGC | TTC | ACC | GGC | TGG | CAG | TGG | GTG | CTA | AGC | GCG | 915 |
| Val | Val | Pro | Ala | Thr 125 | Arg | Phe | Thr | Gly | Trp 130 | Gln | Trp | Val | Leu | Ser 135 | Ala | |
| CTG | GCA | CTG | CCG | GTC | GTG | ACC | TGG | GCG | GCG | TGG | CCG | TTT | CAC | CGC | GTT | 963 |
| Leu | Ala | Leu | Pro 140 | Val | Val | Thr | Trp | Ala 145 | Ala | Trp | Pro | Phe | His 150 | Arg | Val | |
| GCG | ATG | CGC | AAC | GCC | CGC | CAC | CAC | GCC | GCC | TCC | ATG | GAG | ACG | CTA | ATC | 1011 |
| Ala | Met | Arg 155 | Asn | Ala | Arg | His | His 160 | Ala | Ala | Ser | Met | Glu 165 | Thr | Leu | Ile | |
| TCG | GTC | GGT | ATC | ACG | GCC | GCC | ACG | ATC | TGG | TCG | CTG | TAC | ACC | GTC | TTC | 1059 |
| Ser | Val 170 | Gly | Ile | Thr | Ala | Ala 175 | Thr | Ile | Trp | Ser | Leu 180 | Tyr | Thr | Val | Phe | |
| GGC | AAT | CAC | TCG | CCC | ATC | GAG | CGC | AGC | GGC | ATA | TGG | CAG | GCG | CTG | CTG | 1107 |
| Gly 185 | Asn | His | Ser | Pro | Ile 190 | Glu | Arg | Ser | Gly | Ile 195 | Trp | Gln | Ala | Leu | Leu 200 | |
| GGA | AGC | GAT | GCT | ATT | TAT | TTC | GAG | GTC | GCG | GCG | GGT | GTC | ACG | GTG | TTC | 1155 |
| Gly | Ser | Asp | Ala | Ile 205 | Tyr | Phe | Glu | Val | Ala 210 | Ala | Gly | Val | Thr | Val 215 | Phe | |
| GTG | CTG | GTG | GGG | CGG | TAT | TTC | GAG | GCG | CGC | GCC | AAG | TCG | CAG | GCG | GGC | 1203 |
| Val | Leu | Val | Gly 220 | Arg | Tyr | Phe | Glu | Ala 225 | Arg | Ala | Lys | Ser | Gln 230 | Ala | Gly | |
| AGT | GCG | CTG | AGA | GCC | TTG | GCG | GCG | CTG | AGC | GCC | AAG | GAA | GTA | GCC | GTC | 1251 |
| Ser | Ala | Leu 235 | Arg | Ala | Leu | Ala | Ala 240 | Leu | Ser | Ala | Lys | Glu 245 | Val | Ala | Val | |
| CTG | CTA | CCG | GAT | GGG | TCG | GAG | ATG | GTC | ATC | CCG | GCC | GAC | GAA | CTC | AAA | 1299 |
| Leu | Leu 250 | Pro | Asp | Gly | Ser | Glu 255 | Met | Val | Ile | Pro | Ala 260 | Asp | Glu | Leu | Lys | |
| GAA | CAG | CAG | CGC | TTC | GTG | GTG | CGT | CCA | GGG | CAG | ATA | GTT | GCC | GCC | GAC | 1347 |
| Glu 265 | Gln | Gln | Arg | Phe | Val 270 | Val | Arg | Pro | Gly | Gln 275 | Ile | Val | Ala | Ala | Asp 280 | |
| GGC | CTC | GCC | GTC | GAC | GGG | TCC | GCT | GCG | GTC | GAC | ATG | AGC | GCG | ATG | ACC | 1395 |
| Gly | Leu | Ala | Val | Asp 285 | Gly | Ser | Ala | Ala | Val 290 | Asp | Met | Ser | Ala | Met 295 | Thr | |
| GGC | GAG | GCC | AAA | CCG | ACC | CGG | GTG | CGT | CCG | GGG | GGG | CAG | GTC | ATC | GGC | 1443 |
| Gly | Glu | Ala | Lys 300 | Pro | Thr | Arg | Val | Arg 305 | Pro | Gly | Gly | Gln | Val 310 | Ile | Gly | |
| GGC | ACC | ACA | GTG | CTT | GAC | GGC | CGG | CTG | ATC | GTG | GAG | GCG | GCC | GCG | GTG | 1491 |
| Gly | Thr | Thr 315 | Val | Leu | Asp | Gly | Arg 320 | Leu | Ile | Val | Glu | Ala 325 | Ala | Ala | Val | |
| GGC | GCC | GAC | ACC | CAG | TTC | GCC | GGA | ATG | GTC | CGC | CTC | GTT | GAG | CAA | GCG | 1539 |
| Gly | Ala | Asp 330 | Thr | Gln | Phe | Ala | Gly 335 | Met | Val | Arg | Leu | Val 340 | Glu | Gln | Ala | |
| CAG | GCG | CAA | AAG | GCC | GAC | GCA | CAG | CGA | CTA | GCC | GAC | CGG | ATC | TCC | TCG | 1587 |
| Gln | Ala | Gln | Lys 345 | Ala | Asp | Ala | Gln | Arg 350 | Leu | Ala | Asp | Arg | Ile 355 | Ser | Ser 360 | |
| GTG | TTT | GTT | CCC | GCT | GTG | TTG | GTT | ATC | GCG | GCA | CTA | ACC | GCA | GCC | GGA | 1635 |
| Val | Phe | Val | Pro | Ala 365 | Val | Leu | Val | Ile | Ala 370 | Ala | Leu | Thr | Ala | Ala 375 | Gly | |
| TGG | CTA | ATC | GCC | GGG | GGA | CAA | CCC | GAC | CGT | GCC | GTC | TCG | GCC | GCA | CTC | 1683 |
| Trp | Leu | Ile | Ala 380 | Gly | Gly | Gln | Pro | Asp 385 | Arg | Ala | Val | Ser | Ala 390 | Ala | Leu | |

| | | | | | | | | | | | | | | | | |
|---|---|---|---|---|---|---|---|---|---|---|---|---|---|---|---|---|
| GCC | GTG | CTT | GTC | ATC | GCC | TGC | CCG | TGT | GCC | CTG | GGG | CTG | GCG | ACT | CCG | 1731 |
| Ala | Val | Leu | Val | Ile | Ala | Cys | Pro | Cys | Ala | Leu | Gly | Leu | Ala | Thr | Pro | |
| | | 395 | | | | 400 | | | | | | 405 | | | | |
| ACC | GCG | ATG | ATG | GTG | GCC | TCT | GGT | CGC | GGT | GCC | CAG | CTC | GGA | ATA | TTT | 1779 |
| Thr | Ala | Met | Met | Val | Ala | Ser | Gly | Arg | Gly | Ala | Gln | Leu | Gly | Ile | Phe | |
| | 410 | | | | | 415 | | | | | 420 | | | | | |
| CTG | AAG | GGC | TAC | AAA | TCG | TTG | GAG | GCC | ACC | CGC | GCG | GTG | GAC | ACC | GTC | 1827 |
| Leu | Lys | Gly | Tyr | Lys | Ser | Leu | Glu | Ala | Thr | Arg | Ala | Val | Asp | Thr | Val | |
| 425 | | | | | 430 | | | | | 435 | | | | | 440 | |
| GTC | TTC | GAC | AAG | ACC | GGC | ACC | CTG | ACG | ACG | GGC | CGG | CTG | CAG | GTC | AGT | 1875 |
| Val | Phe | Asp | Lys | Thr | Gly | Thr | Leu | Thr | Thr | Gly | Arg | Leu | Gln | Val | Ser | |
| | | | | 445 | | | | | 450 | | | | | 455 | | |
| GCG | GTG | ACC | GCG | GCA | CCG | GGC | TGG | GAG | GCC | GAC | CAG | GTG | CTC | GCC | TTG | 1923 |
| Ala | Val | Thr | Ala | Ala | Pro | Gly | Trp | Glu | Ala | Asp | Gln | Val | Leu | Ala | Leu | |
| | | | 460 | | | | | 465 | | | | | 470 | | | |
| GCC | GCG | ACC | GTG | GAA | GCC | GCG | TCC | GAG | CAC | TCG | GTG | GCG | CTC | GCG | ATC | 1971 |
| Ala | Ala | Thr | Val | Glu | Ala | Ala | Ser | Glu | His | Ser | Val | Ala | Leu | Ala | Ile | |
| | | 475 | | | | | 480 | | | | | 485 | | | | |
| GCC | GCG | GCA | ACG | ACT | CGG | CGA | GAC | GCG | GTC | ACC | GAC | TTT | CGC | GCC | ATA | 2019 |
| Ala | Ala | Ala | Thr | Thr | Arg | Arg | Asp | Ala | Val | Thr | Asp | Phe | Arg | Ala | Ile | |
| | 490 | | | | | 495 | | | | | 500 | | | | | |
| CCC | GGC | CGC | GGC | GTC | AGC | GGC | ACC | GTG | TCC | GGG | CGG | GCG | GTA | CGG | GTG | 2067 |
| Pro | Gly | Arg | Gly | Val | Ser | Gly | Thr | Val | Ser | Gly | Arg | Ala | Val | Arg | Val | |
| 505 | | | | | 510 | | | | | 515 | | | | | 520 | |
| GGC | AAA | CCG | TCA | TGG | ATC | GGG | TCC | TCG | TCG | TGC | CAC | CCC | AAC | ATG | CGC | 2115 |
| Gly | Lys | Pro | Ser | Trp | Ile | Gly | Ser | Ser | Ser | Cys | His | Pro | Asn | Met | Arg | |
| | | | | 525 | | | | | 530 | | | | | 535 | | |
| GCG | GCC | CGG | CGC | CAC | GCC | GAA | TCG | CTG | GGT | GAG | ACG | GCC | GTA | TTC | GTC | 2163 |
| Ala | Ala | Arg | Arg | His | Ala | Glu | Ser | Leu | Gly | Glu | Thr | Ala | Val | Phe | Val | |
| | | | 540 | | | | | 545 | | | | | 550 | | | |
| GAG | GTC | GAC | GGC | GAA | CCA | TGC | GGG | GTC | ATC | GCG | GTC | GCC | GAC | GCC | GTC | 2211 |
| Glu | Val | Asp | Gly | Glu | Pro | Cys | Gly | Val | Ile | Ala | Val | Ala | Asp | Ala | Val | |
| | | 555 | | | | | 560 | | | | | 565 | | | | |
| AAG | GAC | TCG | GCG | CGA | GAC | GCC | GTG | GCC | GCC | CTG | GCC | GAT | CGT | GGT | CTG | 2259 |
| Lys | Asp | Ser | Ala | Arg | Asp | Ala | Val | Ala | Ala | Leu | Ala | Asp | Arg | Gly | Leu | |
| | 570 | | | | | 575 | | | | | 580 | | | | | |
| CGC | ACC | ATG | CTG | TTG | ACC | GGT | GAC | AAT | CCC | GAA | TCG | GCG | GCG | GCC | GTG | 2307 |
| Arg | Thr | Met | Leu | Leu | Thr | Gly | Asp | Asn | Pro | Glu | Ser | Ala | Ala | Ala | Val | |
| 585 | | | | | 590 | | | | | 595 | | | | | 600 | |
| GCT | ACT | CGC | GTC | GGC | ATC | GAC | GAG | GTG | ATC | GCC | GAC | ATC | CTG | CCG | GAA | 2355 |
| Ala | Thr | Arg | Val | Gly | Ile | Asp | Glu | Val | Ile | Ala | Asp | Ile | Leu | Pro | Glu | |
| | | | | 605 | | | | | 610 | | | | | 615 | | |
| GGC | AAG | GTC | GAT | GTC | ATC | GAG | CAG | CTA | CGC | GAC | CGC | GGA | CAT | GTC | GTC | 2403 |
| Gly | Lys | Val | Asp | Val | Ile | Glu | Gln | Leu | Arg | Asp | Arg | Gly | His | Val | Val | |
| | | | 620 | | | | | 625 | | | | | 630 | | | |
| GCC | ATG | GTC | GGT | GAC | GGC | ATC | AAC | GAC | GGA | CCC | GCA | CTG | GCC | CGT | GCC | 2451 |
| Ala | Met | Val | Gly | Asp | Gly | Ile | Asn | Asp | Gly | Pro | Ala | Leu | Ala | Arg | Ala | |
| | | 635 | | | | | 640 | | | | | 645 | | | | |
| GAT | CTA | GGC | ATG | GCC | ATC | GGG | CGC | GGC | ACG | GAC | GTC | GCG | ATC | GGT | GCC | 2499 |
| Asp | Leu | Gly | Met | Ala | Ile | Gly | Arg | Gly | Thr | Asp | Val | Ala | Ile | Gly | Ala | |
| | 650 | | | | | 655 | | | | | 660 | | | | | |
| GCC | GAC | ATC | ATC | TTG | GTC | CGC | GAC | CAC | CTC | GAC | GTT | GTA | CCC | CTT | GCG | 2547 |
| Ala | Asp | Ile | Ile | Leu | Val | Arg | Asp | His | Leu | Asp | Val | Val | Pro | Leu | Ala | |
| 665 | | | | | 670 | | | | | 675 | | | | | 680 | |
| CTT | GAC | CTG | GCA | AGG | GCC | ACG | ATG | CGC | ACC | GTC | AAA | CTC | AAC | ATG | GTC | 2595 |
| Leu | Asp | Leu | Ala | Arg | Ala | Thr | Met | Arg | Thr | Val | Lys | Leu | Asn | Met | Val | |
| | | | | 685 | | | | | 690 | | | | | 695 | | |
| TGG | GCA | TTC | GGA | TAC | AAC | ATC | GCC | GCG | ATT | CCC | GTC | GCC | GCT | GCC | GGA | 2643 |
| Trp | Ala | Phe | Gly | Tyr | Asn | Ile | Ala | Ala | Ile | Pro | Val | Ala | Ala | Ala | Gly | |
| | | | 700 | | | | | 705 | | | | | 710 | | | |

| CTG | CTC | AAC | CCC | CTG | GTG | GCC | GGT | GCG | GCC | ATG | GCG | TTC | TCA | TCG | TTC | 2691 |
| Leu | Leu | Asn | Pro | Leu | Val | Ala | Gly | Ala | Ala | Met | Ala | Phe | Ser | Ser | Phe | |
| | | 715 | | | | 720 | | | | | | 725 | | | | |

| TTC | GTG | GTC | TCA | AAC | AGC | TTG | CGG | TTG | CGC | AAA | TTT | GGG | CGA | TAC | CCG | 2739 |
| Phe | Val | Val | Ser | Asn | Ser | Leu | Arg | Leu | Arg | Lys | Phe | Gly | Arg | Tyr | Pro | |
| | 730 | | | | | 735 | | | | | 740 | | | | | |

| CTA | GGC | TGC | GGA | ACC | GTC | GGT | GGG | CCA | CAA | ATG | ACC | GCG | CCG | TCG | TCC | 2787 |
| Leu | Gly | Cys | Gly | Thr | Val | Gly | Gly | Pro | Gln | Met | Thr | Ala | Pro | Ser | Ser | |
| 745 | | | | | 750 | | | | | 755 | | | | | 760 | |

GCG TGATGCGTTG TCGGGCAACA CGATATCGGG CTCAGCGGCG ACCGCATCCG 2840
Ala

GTCTCGGCCG AGGACCAGAG GCGCTTCGCC ACACCATGAT TGCCAGGACC GCGCCGATCA 2900

CCACCGGCAG ATGAGTCAAA ATCCGCGTGG TGCTGACCGC GCCGGACAGC GCATCCACAA 2960

TCACATAGCC GGTCAGTATG GCGACGAACG CCGTCAGAAC ACCGGCCAGG CCGGCGGCGG 3020

CGCTCGGCCA TAGCGCCGCG CCCACCATGA TCACACCGAG CGCAATCGAC CACGACGTGA 3080

CTCGTTGAGC AAGTGGGTGC CGGCACCCGT CGGGTGCTGA TGGGTCAGGC CGACGTCTAG 3140

GCCAAACCCC TGCACGGTGC CCAGGGCGAT CTGCGCGATG CCCACGCACA GCAACGCCCA 3200

ACGTCGCCAG GTCATCGGTG AATGTTGCCG CCGCGGCGCC CGGCGGATCC 3250

( 2 ) INFORMATION FOR SEQ ID NO:2:

( i ) SEQUENCE CHARACTERISTICS:
        ( A ) LENGTH: 761 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

| Met | Thr | Ala | Ala | Val | Thr | Gly | Glu | His | His | Ala | Ser | Val | Gln | Arg | Ile |
| 1 | | | | 5 | | | | | 10 | | | | | 15 | |

| Gln | Leu | Arg | Ile | Ser | Gly | Met | Ser | Cys | Ser | Ala | Cys | Ala | His | Arg | Val |
| | | | 20 | | | | 25 | | | | | 30 | | | |

| Glu | Ser | Thr | Leu | Asn | Lys | Leu | Pro | Gly | Val | Arg | Ala | Ala | Val | Asn | Phe |
| | | 35 | | | | | 40 | | | | | 45 | | | |

| Gly | Thr | Arg | Val | Ala | Thr | Ile | Asp | Thr | Ser | Glu | Ala | Val | Asp | Ala | Ala |
| | 50 | | | | | 55 | | | | | 60 | | | | |

| Ala | Leu | Cys | Gln | Ala | Val | Arg | Arg | Ala | Gly | Tyr | Gln | Ala | Asp | Leu | Cys |
| 65 | | | | | 70 | | | | | 75 | | | | | 80 |

| Thr | Asp | Asp | Gly | Arg | Ser | Ala | Ser | Asp | Pro | Asp | Ala | Asp | His | Ala | Arg |
| | | | | 85 | | | | | 90 | | | | | 95 | |

| Gln | Leu | Leu | Ile | Arg | Leu | Ala | Ile | Ala | Ala | Val | Leu | Phe | Val | Pro | Val |
| | | | 100 | | | | 105 | | | | | 110 | | | |

| Ala | Asp | Leu | Ser | Val | Met | Phe | Gly | Val | Val | Pro | Ala | Thr | Arg | Phe | Thr |
| | | | 115 | | | | 120 | | | | | 125 | | | |

| Gly | Trp | Gln | Trp | Val | Leu | Ser | Ala | Leu | Ala | Leu | Pro | Val | Val | Thr | Trp |
| | 130 | | | | | 135 | | | | | 140 | | | | |

| Ala | Ala | Trp | Pro | Phe | His | Arg | Val | Ala | Met | Arg | Asn | Ala | Arg | His | His |
| 145 | | | | | 150 | | | | | 155 | | | | | 160 |

| Ala | Ala | Ser | Met | Glu | Thr | Leu | Ile | Ser | Val | Gly | Ile | Thr | Ala | Ala | Thr |
| | | | | 165 | | | | | 170 | | | | | 175 | |

| Ile | Trp | Ser | Leu | Tyr | Thr | Val | Phe | Gly | Asn | His | Ser | Pro | Ile | Glu | Arg |
| | | | 180 | | | | 185 | | | | | 190 | | | |

| Ser | Gly | Ile | Trp | Gln | Ala | Leu | Leu | Gly | Ser | Asp | Ala | Ile | Tyr | Phe | Glu |
| | | | 195 | | | | 200 | | | | | 205 | | | |

```
Val Ala Ala Gly Val Thr Val Phe Val Leu Val Gly Arg Tyr Phe Glu
    210             215                 220
Ala Arg Ala Lys Ser Gln Ala Gly Ser Ala Leu Arg Ala Leu Ala Ala
225                 230                 235                 240
Leu Ser Ala Lys Glu Val Ala Val Leu Leu Pro Asp Gly Ser Glu Met
            245                 250                 255
Val Ile Pro Ala Asp Glu Leu Lys Glu Gln Gln Arg Phe Val Val Arg
            260                 265                 270
Pro Gly Gln Ile Val Ala Ala Asp Gly Leu Ala Val Asp Gly Ser Ala
            275             280                 285
Ala Val Asp Met Ser Ala Met Thr Gly Glu Ala Lys Pro Thr Arg Val
    290             295                 300
Arg Pro Gly Gly Gln Val Ile Gly Gly Thr Thr Val Leu Asp Gly Arg
305             310                 315                 320
Leu Ile Val Glu Ala Ala Ala Val Gly Ala Asp Thr Gln Phe Ala Gly
                325             330                 335
Met Val Arg Leu Val Glu Gln Ala Ala Gln Lys Ala Asp Ala Gln
            340                 345                 350
Arg Leu Ala Asp Arg Ile Ser Ser Val Phe Val Pro Ala Val Leu Val
            355             360                 365
Ile Ala Ala Leu Thr Ala Ala Gly Trp Leu Ile Ala Gly Gly Gln Pro
    370                 375                 380
Asp Arg Ala Val Ser Ala Ala Leu Ala Val Leu Val Ile Ala Cys Pro
385                 390                 395                 400
Cys Ala Leu Gly Leu Ala Thr Pro Thr Ala Met Met Val Ala Ser Gly
            405                 410                 415
Arg Gly Ala Gln Leu Gly Ile Phe Leu Lys Gly Tyr Lys Ser Leu Glu
            420                 425                 430
Ala Thr Arg Ala Val Asp Thr Val Phe Asp Lys Thr Gly Thr Leu
        435             440                 445
Thr Thr Gly Arg Leu Gln Val Ser Ala Val Thr Ala Ala Pro Gly Trp
    450                 455                 460
Glu Ala Asp Gln Val Leu Ala Leu Ala Ala Thr Val Glu Ala Ala Ser
465                 470                 475                 480
Glu His Ser Val Ala Leu Ala Ile Ala Ala Ala Thr Thr Arg Arg Asp
                485                 490                 495
Ala Val Thr Asp Phe Arg Ala Ile Pro Gly Arg Gly Val Ser Gly Thr
            500                 505                 510
Val Ser Gly Arg Ala Val Arg Val Gly Lys Pro Ser Trp Ile Gly Ser
            515                 520                 525
Ser Ser Cys His Pro Asn Met Arg Ala Ala Arg Arg His Ala Glu Ser
        530                 535                 540
Leu Gly Glu Thr Ala Val Phe Val Glu Val Asp Gly Glu Pro Cys Gly
545                 550                 555                 560
Val Ile Ala Val Ala Asp Ala Val Lys Asp Ser Ala Arg Asp Ala Val
                565                 570                 575
Ala Ala Leu Ala Asp Arg Gly Leu Arg Thr Met Leu Leu Thr Gly Asp
            580                 585                 590
Asn Pro Glu Ser Ala Ala Ala Val Ala Thr Arg Val Gly Ile Asp Glu
        595                 600                 605
Val Ile Ala Asp Ile Leu Pro Glu Gly Lys Val Asp Val Ile Glu Gln
    610                 615                 620
Leu Arg Asp Arg Gly His Val Val Ala Met Val Gly Asp Gly Ile Asn
625                 630                 635                 640
```

| | | | | | | | | | | | | | | |
|---|---|---|---|---|---|---|---|---|---|---|---|---|---|---|
| Asp | Gly | Pro | Ala | Leu 645 | Ala | Arg | Ala | Asp | Leu 650 | Gly | Met | Ala | Ile | Gly 655 | Arg |
| Gly | Thr | Asp | Val 660 | Ala | Ile | Gly | Ala | Ala 665 | Asp | Ile | Ile | Leu | Val 670 | Arg | Asp |
| His | Leu | Asp 675 | Val | Val | Pro | Leu | Ala 680 | Leu | Asp | Leu | Ala | Arg 685 | Ala | Thr | Met |
| Arg | Thr 690 | Val | Lys | Leu | Asn | Met 695 | Val | Trp | Ala | Phe | Gly 700 | Tyr | Asn | Ile | Ala |
| Ala 705 | Ile | Pro | Val | Ala | Ala 710 | Ala | Gly | Leu | Leu | Asn 715 | Pro | Leu | Val | Ala | Gly 720 |
| Ala | Ala | Met | Ala | Phe 725 | Ser | Ser | Phe | Phe | Val 730 | Val | Ser | Asn | Ser | Leu 735 | Arg |
| Leu | Arg | Lys | Phe 740 | Gly | Arg | Tyr | Pro | Leu 745 | Gly | Cys | Gly | Thr | Val 750 | Gly | Gly |
| Pro | Gln | Met 755 | Thr | Ala | Pro | Ser | Ser 760 | Ala | | | | | | | |

NUCLEIC ACIDS ENCODING MEMBRANE-ASSOCIATED IMMUNOGENS OF MYCOBACTERIAL AND CORRESPONDING PROBES, VECTORS, AND TRANSFORMED HOST CELLS

This is a division, of application Ser. No. 07/906,395 filed Jun. 29, 1992, now U.S. Pat. No. 5,330,754.

TECHNICAL FIELD OF THE INVENTION

The invention relates to membrane-associated polypeptides of mycobacteria and, in particular, the use of such polypeptides and the nucleic acids encoding them for use as vaccines and diagnostic reagents.

BACKGROUND OF THE INVENTION

The mycobacteria are a diverse collection of acid fast, gram-positive bacteria, some of which cause important human and animal diseases. In humans, the two most common mycobacteria-caused diseases are tuberculosis (TB) and leprosy, which result from infection with *M. tuberculosis* and *M. leprae*, respectively.

Tuberculosis displays all of the principal characteristics of a global epidemic disease. Currently, tuberculosis afflicts more than 35 million individuals worldwide and results in over 4 million deaths annually. In India, at any given time, almost 8 million people are reported to suffer from this disease and 500,000 deaths recorded. These figures may not cover the totality of those suffering from this disease in this country. Thus, tuberculosis appears to be a problem of major concern in India as also in many other countries of the world.

Tuberculosis is caused by *M. tuberculosis, M. bovis, africanum* and *M. microti*, the acid-fast, Gram positive, tubercle bacilli of the family Mycobacteriaceae. Some local pathogenic strains of *M. tuberculosis* have also been isolated from patients in Madras and other cities in India, which differ in some respects from *M. tuberculosis* H37Rv, which is a virulent strain.

In recent years, certain groups of individuals with AIDS have been found to have a markedly increased incidence of TB as well. It has now been shown that one group of mycobacteria which consists of *M. avium, M. intracellulare* and *M. scrofulaceum*, jointly known as MAIS complex, is responsible for disseminated disease in a large number of persons with AIDS (Kiehn et al., *J. Clin. Microbiol.*, 21:168–173 (1985); Wong et al., *Amer. J. Med.*, 78:35–40 (1985)).

Since Koch identified *M. tuberculosis* as the causative agent of tuberculosis in 1882, many scientific studies and public health efforts have been directed at diagnosis, treatment and control of this disease. However, characteristics of *M. tuberculosis* have hampered research to improve diagnosis and to develop more effective vaccines. In addition, the biochemical composition of the organism has made identification and purification of the cellular constituents difficult, and many of these materials once purified, lack sensitivity and specificity as diagnostic reagents. As a result, diagnostic and immunoprophylactic measures for mycobacterial diseases have changed little in the past half century. The conventional methods for the diagnosis of *M. tuberculosis* are troublesome and results are delayed.

Bacillus Calmette-Guerin (BCG), an avirulent strain of *M. bovis* (Calmette, A., Masson et Cie, Paris (1936)), is used extensively as a vaccine against tuberculosis. Though numerous studies have found that it has protective efficacy against tuberculosis (Luelmo, F., *Am. Rev. Respir. Dis.*, 125, 70–72 (1982)) BCG has failed to protect against tuberculosis in several trials (WHO, *Tech. Rep. Ser.*, 651:1–15 (1980)) for reasons that are not entirely clear (Fine, P., *Tubercle*, 65:137–153 (1984); Fine, et al., *Lancet*, (ii) :499–502 (1986)).

The eradication with vaccination, early diagnosis, and efficient therapy is an important objective of the drive to combat mycobacterioses. The lacunae in the present knowledge of the biology of these pathogens—their make-up, their natural history, their physiology, biochemistry and immunological reactivities, highlights the need for attempts to unravel their weaknesses, so that more efficient ways to combat this disease can be devised. To develop more effective tools for the diagnosis and prevention of these diseases, it is important to understand the immune response to infection by mycobacterial pathogens. The mycobacterial components that are important in eliciting the cellular immune response are not yet well defined. The antibody and T-cell responses to infection or inoculation with killed mycobacteria have been studied in humans and in animals. Human patients with TB or leprosy produce serum antibodies directed against mycobacterial antigens. Although antibodies may have some function in the antimycobacterial immune response, the exact function remains to be clarified since no protective role can be ascribed to these antibodies. Protection against mycobacterial diseases involves cell-mediated immunity.

Mycobacteria do not produce any directly toxic substances and consequently their pathogenicity results from multiple factors involved in their interaction with the infected host. Intracellular parasitism probably depends on host cell trophic factors; it is conceivable that their short supply may be bacteriostatic and could play a role in the mechanism of mycobacterial dormancy.

It is generally understood that protective immunity in mycobacterial infection is mediated by specific T cells which activate macrophages into non-specific tuberculocidal activity. Evidence suggests that gamma-IFN triggers macrophages towards $H_2O_2$-mediated bacterial killing, but related or other macrophage activating factor (MAF) molecules may also be involved. The causes responsible for the inadequate bactericidal function at sites of abundant T cell proliferation have not yet been explained. Dissociation between delayed-type hypersensitivity (DTH) and protective immunity led to views that T-cells of a distinct subset or specificity could be responsible for the acquired resistance to mycobacterial infection. Alternatively, interference with protection may result from corollary cellular reactions, namely by suppressor T-cells and macrophages, or from the shifting of T-cells towards helper function for B-cells.

Unlike viral and some parasite pathogens which can evade host resistance by antigenic shift, mycobacteria have a resilient cell wall structure and can suppress host immune responses by the action of their immunomodulatory cell wall constituents. Whilst the success of protective immunization towards other microbial pathogens mainly depends on quantitative parameters of immunity, it appears that mycobacterial immunomodulatory stimuli produce a regulatory dysfunction of the host immune system. This may not be possible to override simply by more resolute immunization using vaccines of complex composition such as whole mycobacteria (e.g. BCG). Perhaps mycobacteria did not evolve potent "adjuvant" structures to boost the host immunity but rather to subvert host defenses towards ineffective cellular reactions operating to the advantage of the pathogen.

Vaccination with an attenuated pathogen such as BCG could amplify further immune responses but with limited protection of the host, the potential scope for immunization with defined antigens is yet to be explored.

The purification and characterization of individual antigenic proteins are essential in understanding the fundamental mechanism of the DTH reaction on the molecular level. The possible functional role of proteins of defined structure in the pathogenesis of mycobacterial diseases as well as for diagnostic purposes remains of great interest. Numerous groups have attempted to define mycobacterial antigens by standard biochemical and immunological techniques, and common as well as species specific antigens have been reported in mycobacteria (Minden, et al., *Infect. Immun.*, 46:519–525 (1984); Closs, et al., *Scand. J. Immunol.*, 12:249–263 (1980); Chaparas, et al., *Am. Rev. Respir. Dis.*, 122:533 (1980); Daniel, et al., *Microbiol. Rev.*, 42:84–113 (1978); Stanford, et al., *Tubercle*, 55:143–152 (1974); Kuwabara, S., *J. Biol. Chem.*, 250:2556–2562 (1975)).

Very little information about the mycobacterial genome is available. Initially, basic studies were conducted to estimate the genome size, G+C content and the degree of DNA homology between the various mycobacterial genomes (Grosskinsky, et al., *Infect. Immun.*, 57, 5:1535–1541 (1989); Garcia, et al., *J. Gen. Microbiol.*, 132:2265–2269 (1986); Imaeda, T., *Int. J. Sys. Bacteriol.*, 35, 2:147–150 (1985); Clark-Curtiss, et al., *J. Bacteriol.*, 161 3:1093–1102 (1985); Baess, I. et al., B., *Acta. Path. Microbiol. Scand.*, (1978) 86:309–312; Bradley, S. G., *Am. Rev. Respir. Dis.*, 106:122–124 (1972)). Recently, recombinant DNA techniques have been used for the cloning and expression of mycobacterial genes. Genomic DNA fragments of *M. tuberculosis, M. leprae* and some other mycobacterial species were used for the construction of lambda gt11 phage (Young, et al., *Proc. Natl. Acad. Sci.*, U.S.A., 82:2583–2587 (1985); Young, et al., *Nature* (London), 316:450–452 (1985)) or other vector-based recombinant gene libraries. These libraries were screened with murine monoclonal antibodies (Engers, et al., *Infect. Immun.*, 48:603–605 (1985); Engers, et al., *Infect. Immun.*, 51:718–720 (1986)) as well as polyclonal antisera and some immunodominant antigens were identified. The principal antigen among these being five 12, 14, 19, 65 & 71 kDa of *M. tuberculosis* (Young et al., *Proc. Natl. Acad. Sci.*, U.S.A., 82:2583–2587 (1985); Shinnick et al., *Infect. Immun.*, 55(7):1718–1721 (1987); Husson and Young, Proc. Natl. Sc. Acad., 84:1679–1683 (1987); and five 12, 18, 23, 36& 65 kDa antigens of *M. leprae* (Young, et al., *Nature* (London), 316:450–452 (1985)). A few homologues of some of these antigens were also identified in some other mycobacterial species (e.g., BCG) (Yamaguchi et al., FEB 06511, 240:115–117 (1988); Yamaguchi et al., *Infect. Immun.*, 57:283–288 (1989); Matsuo, et al., *J. Bacteriol.*, 170, 9:3847–3854 (1988); Radford, et al., *Infect. Immun.*, 56, 4:921–925 (1988); Lu, et al., *Infect. Immun.*, 55, 10:2378–2382 (1987); Minden, et al., *Infect. Immun.*, 53, 3:560–564 (1986); Harboe, et al., *Infect. Immun.*, 52, 1:293–302 (1986); Thole, et al., *Infect. Immun.*, 50, 3:800–806 (1985)). These antigens, however, are either intracellular or secreted molecules. Although *M. bovis* BCG has been widely used as a vaccine against tuberculosis, the determination of the membrane-associated polypeptides of mycobacterium that are capable of inducing a protective immune response is highly desirable. The use of such a membrane-associated polypeptide or the DNA encoding it provides for the generation of recombinant vaccines, e.g., mycobacterial membrane-associated immunogens expressed in, for example, a virus or bacterium such as vaccinia virus, Salmonella, etc. used as a live carrier, or the display of non-mycobacterial immunogens on the surface of a cultivable mycobacterial strain which can be used as a live recombinant vaccine.

Accordingly, it is an object herein to provide methods for identifying and isolating nucleic acids encoding a membrane-associated polypeptide of mycobacteria.

Further, it is an object herein to provide membrane-associated polypeptides of mycobacteria and the nucleic acids encoding it.

Still further, it is an object herein to provide vaccines utilizing all or part of the membrane-associated polypeptide of a mycobacterium or the DNA encoding such membrane-associated polypeptide.

Still further, it is an object to provide reagents comprising said membrane-associated polypeptide with a mycobacterium or DNA encoding it useful in diagnostic assays for mycobacterial infection.

Still further, it is an object to provide a promoter sequence comprising the promoter of said membrane associated polypeptide, which can direct gene expression in mycobacteria as well as in other microorganisms such as *E. coli*.

SUMMARY OF THE INVENTION

In accordance with the foregoing objects, the invention includes compositions comprising nucleic acid encoding all or part of a membrane-associated polypeptide of a mycobacterium and the membrane-associated polypeptide encoded by said DNA. The membrane-associated polypeptide is characterized by the ability to detect an immune response to pathogenic mycobacteria or the mycobacteria from which the membrane associated polypeptide or part thereof is derived. Such mycobacteria include *M. bovis, M. tuberculosis, leprae, M. africanum* and *M. microti, M. avium, M. intracellular* and *M. scrofulaceum* and *M. bovis* BCG.

A particular mycobacterial membrane-associated polypeptide is a 79 kD ion-motive ATPase. Extra-cellular, intra-cellular and transmembrane domains are identified in this mycobacterial membrane-associated polypeptide based upon its DNA and deduced amino acid sequence.

The invention also includes vaccines utilizing all or part of a membrane-associated mycobacterial polypeptide or an expressible form of a nucleic acid encoding it. The invention also includes mycobacterial promoter sequences capable of directing gene expression in mycobacteria as well as in other microorganisms such as *E. coli*. Such promoters are from mycobacterial genes encoding membrane-associated ATPases. A preferred promoter is that of the gene encoding the *M. bovis* BCG 79 kD membrane-associated polypeptide. This promoter sequence is especially useful to express genes of interest in mycobacteria.

BRIEF DESCRIPTION OF THE DRAWINGS

FIGS. 2A and 2B show the comparison of restriction site maps of recombinant clones carrying BCG DNA identified using the immunoscreening assay described herein (FIG. 2B) with the restriction site maps of five immunodominant antigens of *M. tuberculosis* and *M. bovis* BCG genomic DNAs, respectively, (Husson and Young, *Proc. Natl. Acad. Sci.*, U.S.A., 84:1679–1683 (1987); Shinnick et al., *Infect. Immun.*, 55:1718–1721 (1987) (FIG. 2A)). Restriction maps in each panel have been drawn to the same scale (indicated at the top), and restriction sites are indicated above the restriction maps. The dotted line in panel A represents the non-mycobacterial DNA. Restriction enzymes: B, BamHI, E, EcoRI, G, BglII, K, KpnI, P, PvuI, X, XhoI, H,HincII, U, PvuII, Ps, PstI, Hi, HindIII. In panel A, A is SalI and S is SacI. In panel B, S is SalI.

FIGS. 3A–3C illustrates the results of Western blot analysis of the sonicated supernate of recombinant clone pMBB51A which carries a BCG DNA insert identified following immunoscreening of the recombinant colonies. FIG. 3A shows reactivity of MBB51A (lane 2) and *E. coli* (lane 1) with sera from TB patients. FIG. 3B shows reactivity of MBB51A (lanes 1 and 2) and *E. coli* (lane 3) with anti-H37Rv sera raised in rabbits. FIG. 3C shows reactivity of MBB51A (lanes 1 and 2) and *E. coli* (lane 3) with the second antibody alone. Arrows indicate the position of the 90 kD immunoreactive BCG protein expressed by the recombinant MBB51A, which was absent in the negative control.

FIGS. 4A–4E illustrate the nucleotide sequence (Seq. ID No.: 1) of clone pMBB51A 3.25 kb insert DNA containing the *M. bovis* BCG immunoreactive MBB51A gene encoding an ion-motive ATPase, with a deduced molecular weight of 79 kD. The deduced amino acid sequence (Seq. ID No.: 2) is shown below the nucleotide sequence. Upstream promoter elements are underlined. Transcription termination region is indicated by inverted arrows. 5' and 3' flanking regions are also shown.

FIG. 5 illustrates a schematic model derived for the 79 kD protein encoded by pMBB51A which represents an ion-motive ATPase of BCG. The model considers only the structural and functional features that are prominent in the other ion-motive ATPase homologs of transmembrane domains of the protein. Functionally, important amino acid residues are indicated (P), proline at position 400; (D), aspartic acid at position 443; (G), glycine at position 521; and (A), alanine at position 646. Numbers indicate amino acid residues broadly defining the limits of the transmembrane domains.

FIGS. 6A and 6B illustrates the results of Southern blot hybridization of BamHI digest of genomic DNAs from *M. bovis* BCG (lane 6), *M. tuberculosis* H37Rv (lane 5), *M. smegmatis* (lane 4) and *M. vaccae* (lane 3 using pMMB51A DNA insert (lane 8) as probe. FIG. 6A shows ethidium bromide stained gel and FIG. 6B shows the results of Southern blot hybridization.

DETAILED DESCRIPTION OF THE INVENTION

As used herein, a "membrane-associated polypeptide" of a mycobacterium is defined as any Mycobacterial membrane-associated polypeptide which is capable of detecting an immune response against the wild-type mycobacterium containing the membrane-associated polypeptide. However, based upon the observed cross-reactivity of the 79 kD membrane-associated polypeptide of an *M. bovis* BCG with pooled anti-sera from patients afflicted with tuberculosis and the cross-hybridization as between the DNA encoding the 79 kD membrane-associated polypeptide and the DNA of *M. tuberculosis* H37Rv, the membrane-associated polypeptide of the invention is not limited to that identified herein from *M. bovis* BCG. Rather, it encompasses not only homologs to the 79 kD ion-motive ATPase but also any and all membrane-associated polypeptides of a mycobacterium that can be used to detect an immune response by the same or a different mycobacteria in which the membrane-associated polypeptide is normally found.

As used herein, "nucleic acid" includes DNA or RNA as well as modified nucleic acid wherein a detectable label has been incorporated or wherein various modifications have been made to enhance stability, e.g., incorporation of phosphorothioate linkages in the phosphoribose backbone, etc. Such nucleic acid also includes sequences encoding the anti-sense sequence of the DNA encoding the membrane-associated polypeptide such that the now well-known anti-sense technology can be used to modulate expression of such membrane-associated polypeptides.

In some aspects of the invention, the nucleic acid sequence encoding all or part of a membrane-associated polypeptide of the mycobacterium is used as a vaccine. When so-used the nucleic acid is generally an "expressible nucleic acid" that contains all necessary expression regulation sequences to control transcription and translation of the nucleic acid in a designated host system. In some vaccine embodiments, the DNA encodes a chimeric polypeptide containing at least one transmembrane domain of the membrane-associated polypeptide and an "immunogenic polypeptide". The transmembrane domain is used to display the immunogenic polypeptide on the surface of a particular host organism such as an attenuated live vaccine. When the membrane-associated polypeptide includes more than one transmembrane region, one or more of the transmembrane regions can be used with an immunogenic polypeptide. Thus, for example, the 79 kD ion-motive ATPase as shown in FIG. 5 has at least three extracellular domains into which an immunogenic polypeptide can be engineered by well-known methods involving recombinant DNA technology. Although it is preferred that more than one transmembrane region be used to display an immunogenic polypeptide, one skilled in the art can readily vary the length of such a membrane-associated polypeptide to maximize an immunogenic response or to minimize the amount of membrane-associated polypeptide used in such applications.

As used herein, "immunogenic polypeptide" comprises all or part of any polypeptide which can potentially be utilized in a vaccine or diagnostic application. Thus, the immunogenic polypeptide can comprise heterologous immunogens, i.e., immunogens from non-mycobacterial sources, e.g., *Salmonella* or *Shigella* or from different mycobacteria from which the membrane-associated polypeptide is derived, e.g., immunogens from *Mycobacterium tuberculosis* fused to a membrane-associated polypeptide from *M. bovis* BCG. However, in some instances homologous immunogens can be used. For example, each of the extracellular domains as set forth in FIG. 5 herein can be combined and displayed by combination with one or more of the transmembrane domains from the membrane-associated polypeptide normally containing them. Alternatively, the intracellular domains can be displayed extracellularly using appropriate transmembrane regions from the same molecule.

In an alternate vaccine embodiment, all or part of the membrane-associated polypeptide of mycobacteria, rather than the DNA encoding, is used as part of a vaccine. Such proteinaceous vaccines are formulated with well-known adjuvants and administered following well-established protocols known to those skilled in the art.

Figures 1A, 1B:
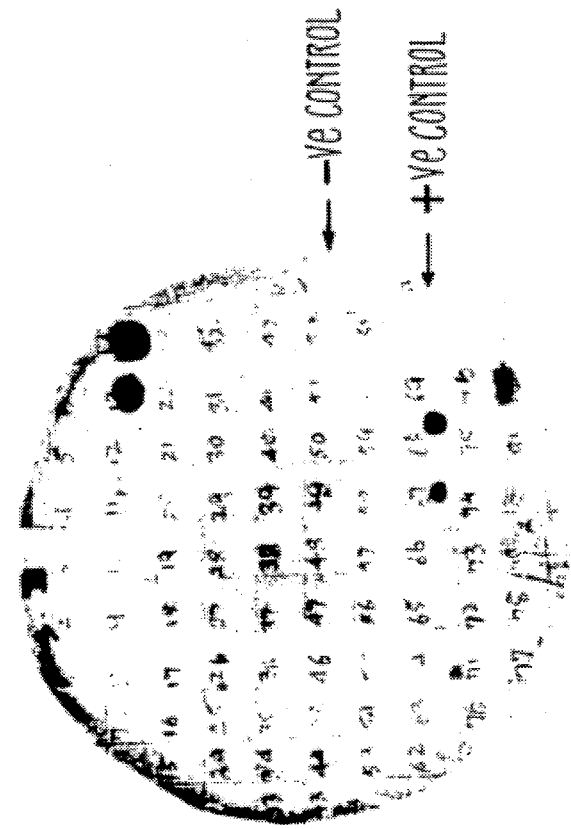
FIGS. 1A and 1B illustrate the results of immunoscreening of recombinant colonies carrying *M. bovis* BCG DNA (FIGS. 1A) and *M. tuberculosis* H37Rv DNA (FIG. 1B), using sera from TB patients in which the presence of *M. bovis* BCG antigens and *M. tuberculosis* H37Rv antigens capable of reacting with the antisera is indicated by a qualitative signal.

In still other embodiments, the nucleic acid encoding the membrane-associated polypeptide of the invention can be used as a diagnostic for detecting infection based upon hybridization with wild-type genes contained by the infectious mycobacterium. Such detection can comprise direct hybridization of DNA extracted from an appropriate diagnostic sample or PCR amplification using the nucleotide sequence of the nucleic acid encoding the membrane-associated polypeptide of the invention to prime amplification. If PCR amplification is primed in a conserved region the presence of mycobacteria in a diagnostic sample can be determined. If primed in a non-conserved region which is species specific the diagnostic assay determined the specific mycobacterium causing an infection.

In addition, the membrane-associated polypeptide of the invention can also be used to detect the presence of antibodies in the sera of patients potentially infected with mycobacteria. Such detection systems include radioimmunoassays and various modifications thereof which are well-know to those skilled in the art. In addition, the membrane-associated polypeptide of the invention can be used to detect the presence of a cell-mediated immune response in a biological sample. Such assay systems are also well-known to those skilled in the art and generally involve the clonal expansion of a sub-population of T cells responding to stimuli from the membrane-associated polypeptide. When so-used, the humoral and/or cell-mediated response of a patient can be determined and monitored over the course of the disease.

Recombinant clones encoding immunogenic protein antigens of *M. bovis* BCG have been isolated from a genomic library of *M. bovis* BCG DNA. In particular, DNA fragments encoding four protein antigens of *M. bovis* BCG have been isolated by probing a pBR322 library of *M. bovis* BCG DNA with sera from TB patients, absorbed on *E. coli*. Restriction site maps of these four recombinant clones are different from those of the five immunodominant antigens of mycobacteria (Young, et al., *Proc. Natl. Acad. Sci.*, U.S.A., 82:2583–2587 (1987); Husson and Young, *Proc. Natl. Acad. Sci.*, U.S.A., 84:1679–1683 (1987); Shinnick et al., *Infect. Immun.*, 55:1718–1721 (1987)), thereby indicating that these cloned protein antigens are novel. One of the recombinant DNA clones encoded an immunoreactive protein with apparent molecular weight of 90 kD as determined by Western blot analysis. The complete nucleotide sequence of the insert DNA of this clone was determined. This clone was found to carry a mycobacterial promoter and a monocistronic ORF encoding a protein of 761 amino acids with a deduced molecular weight of 79 kD. This 79 kD protein had extensive homology with ion-motive ATPases of *S. faecalis* (Solioz et al., *J. Biol. chem*, 262:7358–7362 (1987)), *E. coli* (Hesse et al., *Proc. Natl. Acad. Sci.*, U.S.A., 81:4746–4750 (1984)) and several other organisms, and thus, represents an ion-motive ATPase or a putative K+ATPase of BCG. Using computer algorithms, this ion-motive ATPase was determined to be a membrane protein and has a homologue in *M. tuberculosis* H37Rv, which is pathogenic in humans, but not in *M. vaccae* and *M. smegmatis*, which are non-pathogenic. As a result, novel BCG immunogens can be available which can be useful in the prevention, diagnosis and treatment of tuberculosis and other mycobacterial infections. They can be used, for example, in the development of highly specific serological tests for screening patients for individuals producing antibodies to *M. tuberculosis*, or those infected with *M. tuberculosis*, in the development of vaccines against the disease, and in the assessment of the efficacy of the treatment of infected individuals.

Further, based on the nucleotide sequence of the pMBB51A insert DNA, appropriate oligonucleotide primers can be used for PCR amplification using as template *M. bovis* BCG or *M. tuberculosis* H37Rv DNA. Such a PCR amplification scheme can be thus useful for the detection of mycobacterial DNA in a given sample. Further, by a judicious choice of the primer design, such an amplification procedure can be adapted for taxonomic classification of mycobacterial DNAs. For example, using primers to flank a heavily conserved region such as the ATP-binding site, PCR amplification is common to all mycobacterial species, whereas using primers from non-conserved areas, amplification can be made species specific.

EXAMPLE I

Isolation and Characterization of Genes Encoding Immogenic Protein Antigens of *Mycobacterium bovis* BCG and *Mycobacterium tuberculosis* H37R A. Construction of Recombinant DNA Libraries of *M. bovis* BCG DNA and *Mycobacterium Tuberculosis* H37Rv A recombinant DNA library of *M. bovis* BCG genomic DNA was constructed using pBR322 a high copy number plasmid vector (Bolivar, et al., Gene, 2:95–113 (1977)) with antibiotic markers (ampicillin and tetracycline) and several unique cloning sites. *M. bovis* BCG cells were harvested from a culture in late logarithmic phase of growth and high molecular weight DNA was isolated by the procedure of (Eisenach, et al., *J. Mol. Biol.*, 179:125–142 (1986)) with slight modifications. BCG DNA was digested to completion with BamH I and shotgun cloning of these fragments into the BamH I site of pBR322 was performed. The genomic library was transformed into *E. coli* strain DHI and recombinants were scored on the basis of ampicillin resistance and tetracycline sensitivity. The aim of this approach was to generate restriction fragments of a broad size range so as not to restrict the library to DNA fragments of any particular size range. This cloning strategy also ensured to a large extent that any recombinants selected for expression of mycobacterial antigens should be likely to drive expression from a mycobacterial promoter rather than the Tet promoter of pBR322.

The BCG library constructed in this manner contained 2051 clones of BCG origin. In an analogous manner, a genomic library of Mycobacterium tuberculosis H37Rv DNA was constructed and 1100 clones obtained.

The BCG DNA inserts ranged in size from 0.9 to 9.5 kb. The average size of the mycobacteria DNA fragments inserted in pBR322 was estimated to be about 4 kb. Given the genome size of BCG to be $4.5\times10^3$ kb (Bradley, S. G., *J. Bacteriol.*, 113:645–651 (1973); Imaeda, et al., *Int. J. Syst. Bacteriol.*, 32, 456–458 (1982)), about 1000 clones of this average insert size would represent comprehensively the entire genome of the microorganism.

B. Isolation of Recombinant DNA Clones Encoding BCG *Mycobacterium bovis* BCG and *Mycobacterium tuberculosis* H37Rv Protein Antigens In order to identify recombinants expressing mycobacterial antigens, a colony immunoscreening assay (CIA) to screen recombinant colonies with appropriate antisera, was established. Sera obtained from 20 patients newly diagnosed with active pulmonary tuberculosis were pooled for use in immunoscreening. None of the patients had received treatment for tuberculosis prior to this study and their sputa were positive for acid fast bacteria in all cases. Pooled sera were absorbed on a *E. coli* sonicate overnight at 4° C., to eliminate antibodies cross-reactive to *E. coli* antigens, thereby improving signal to noise ratio during the immunoscreening.

Individual recombinant colonies were grown overnight on nitrocellulose membranes and immunoscreening was carried out as described with slight modifications. The colonies were lysed in chloroform vapor to release the cloned mycobacterial antigens, immobilized on the nitrocellulose paper. The immobilized antigens were reacted with TB sera and binding of the antibody was revealed by standard procedures using a horseradish peroxidase-protein A detection system. The signals obtained with the recombinant clones were compared with that obtained in case of *E. coli* colonies harbouring pBR322 vector alone, which served as the negative control, to assess the signal to noise ratio. Further, to ascertain whether the immunoreactivity of the recombinant clones was due to anti-mycobacterial antibodies or due to a reaction with normal serum components, another CIA of the selected recombinants was performed using TB sera and normal human sera NHS which had been absorbed on *E. coli* in a manner analogous to that described earlier for TB sera. Only those clones reacting selectively with TB sera and not with NHS, were considered to be unambiguously suggestive of the presence of mycobacterial antigens. The use of this immunoscreening approach to identify recombinant colonies carrying mycobacterial DNA inserts capable of expressing mycobacterial antigens is described below:

FIGS. 1A and 1B show the result of immunoscreening of recombinant colonies carrying *M. bovis* BCG DNA (FIG. 1A) or *M. tuberculosis* H37 Rv DNA (FIG. 1B) using sera from TB patients. The colonies were grown on nitrocellulose paper overnight, lysed to release the cloned mycobacterial antigen and allowed to react with the antibodies. The presence of mycobacterial antigen is indicated by a qualitative signal in the recombinant clones which is absent in the negative control comprising colonies harbouring pBR322 vector alone. A similar assay was repeated with normal human serum to ascertain the specificity of the cloned mycobacterial antigens. 51 recombinant colonies carrying *M. bovis* BCG DNA inserts and 45 recombinant colonies carrying *M. tuberculosis* H37Rv DNA inserts were screened by the above procedure; 14 clones of BCG origin (FIG. 1A) and 2 clones of H37Rv origin (FIG. 1B) exhibited distinct strong signals indicating the immunoreactivity of these clones (FIG. 1A–1B). All these clones were also tested for immunoreactivity with NHS. However, with the exception of 3 clones which showed a slight reactivity to NHS, none of the clones reacted with NHS, thereby indicating that these expressed mycobacterial antigens reacted selectively with TB sera. Thus, this procedure resulted in the forthright identification of recombinant clones encoding mycobacterial antigens. This strategy can be generally applicable to mycobacterial gene banks prepared in plasmid or cosmid vectors to identify genes which are expressed in *E. coli* at least to the limit detectable by the immunoassay.

C. Restriction Mapping of Immunoreactive Mycobacterium bovis BCG DNA Recombinants The insert DNAs of four of the immunoreactive BCG recombinant DNA clones isolated using the TB sera were mapped with restriction endonucleases. FIG. 2B shows the genomic DNA restriction site maps deduced for the cloned BCG DNA in four recombinants, in which, A represents Sal I, B, BamH I, E, EcoR I, G, Bgl II, K, Kpn I, P, Pvu I, S, Sac I, X, Xho I. These restriction site maps were then compared with those constructed previously for the five immunodominant antigens of *M. tuberculosis/M. bovis* BCG (Young, et al., *Proc. Natl. Acad. Sci.*, U.S.A., 82:2583–2587 (1985); Husson, et al., *Proc. Natl. Acad. Sci.*, 84:1679–1683 (1987); Shinnick, et al., *Infect. Immun.*, 55, 7:1718–1721 (1987)) (FIG. 2A). Since the restriction site maps shown in FIGS. 2A and 2B have been drawn to the same scale, the differences between the two are apparent. There are no regions of similarity between the restriction site maps of immunoreactive BCG recombinant clones and those of the previously characterized immunodominant antigens of *M. tuberculosis/M. bovis* BCG. Therefore, one can conclude that the cloned BCG DNA inserts in the four recombinants are novel.

EXAMPLE II

Isolation and Characterization of a Gene Encoding a BCG Ion-motive ATPase

A. Identification of a Novel BCG Antigen

One of the four immunoreactive BCG clones, pMBB51A, revealed the presence of a protein of Mr 90 kD, on Western blot analysis using TB sera as well as anti-H37Rv polyclonal antiserum raised in rabbits (FIG. 3). Similar Western blot analysis of pMBB51A with a pool of a few anti-mycobacterial monoclonal antibodies (TB 23, TB 71, TB 72, TB 68, TB 78; Engers et al., *Infec. Immun.*, 48:603–605 (1985)) or with normal human sera did not reveal this immunoreactive protein of 90 kD. This confirms that pMBB51A encodes a BCG antigen which is different from those identified previously in BCG, thereby making it a novel antigen.

B. Determination of the

Nucleotide Sequence of pMBB51A

In order to further characterize this novel BCG antigen, pMBB51A DNA insert was subjected to nucleotide sequencing. The BamH I-BamH I insert carried in pMBB51A was mapped for additional restriction enzyme cleavage sites. It was determined that there were at a minimum a single Pst I site and 3 Sal I sites in this sequence. Overlapping fragments derived from single and double digests of Sal I, BamH I and Sal I, BamH I and Pst I, and Pst I and Sal I, were subcloned into M13mp18 and M13mp19 vectors, in preparation for DNA sequence analysis. DNA sequencing was then carried out using commercially available kits such as the Sequenase system and the T7 system from Pharmacia. Oligonulceotides derived from the determined sequence were synthesized and used as primers to complete the sequence of the larger inserts. Several areas of compression were encountered during the sequencing and these were resolved by using dITP in the sequencing reactions, and by changing the reaction conditions. The complete nucleotide sequence of the pMBB51A insert DNA was determined by sequencing both the strands using dGTP as well as dITP. The DNA sequence of the pMBB51A insert was determined to be 3.25 kb long with a GC content of 67.1% and is shown in FIG. 4.

The determination of the DNA sequence of the 3.25 kb insert of clone pMBB51A (FIGS. 4A–4E) permitted the elucidation of the amino acid sequence of the 90 kD BCG antigen. In FIG. 4, nucleotides are numbered from the left end of the pMBB51A insert DNA.

A search of pMBB51A insert DNA sequence for possible ORFs in all three reading frames revealed the longest ORF of 2286 bp encoding a polypeptide of 761 amino acids on one of the strands. The other strand was found to have a smaller ORF of 1047 bp capable of encoding a polypeptide of 349 amino acids. The longest ORF encoding a 761 amino acid long protein corresponded to a deduced molecular weight of 79 kD which came closest to the immunoreactive BCG protein with apparent molecular weight of 90 kD, seen on the Western blot. The deduced amino acid sequence for this protein is given below the nucleotide sequence in FIG. 4A–4E.

The location of this ORF on the pMBB51A insert DNA was such that there were long stretches of flanking DNA sequences, devoid of any meaningful ORFs, present on either side. This precluded the expression of this ORF from the pBR322 Tet gene promoter and instead suggested that this ORF was being expressed from its own promoter in pMBB51A. This also suggested that E. coli may correctly utilize the M. bovis BCG transcription and translation start and stop sites in this gene.

Immediately upstream of the ORF, regulatory sequences closely matching the −35, −10 and Shine-Dalgarno sequences of E. coli, (Rosenberg, et al., Annul. Rev. Genet., 13:319–353 (1979)) were identified. The spacing between these three regulatory motifs was also very well conserved. Although the other mycobacterial promoters sequenced (Dale, et al., Molecular Biology of the Mycobacteria, chap. 8, 173–198 (1990)) show some differences from the E. coli consensus sequences in all the three regions −35, −10 and SD, the regulatory elements of pMBB51A DNA showed a maximum degree of sequence identity with E. coli in the −35 and SD sequence elements with a single mismatch in each element, and about 50% sequence identity in the Pribnow box. All the above features clearly indicated that this region is the promoter region for the mycobacterial gene contained in pMBB51A. The extent of similarity between this BCG promoter sequence and a typical E. coli promoter is remarkable and explains the functional activity of this promoter, unlike many other mycobacterial promoters, in E. coli. The translation initiation codon in this ORF was ATG at position 508 while a single translation termination codon TGA was identified at position 2790. Potential transcription termination structures capable of forming stem and loop conformations were identified in the region 3' to this ORF. The pMBB51A ORF thus represented a monocistronic gene rather than an operon. The promoter region of MBB51A gene is capable of directing gene expression in E. coli as well as in mycobacteria. This promoter sequence is useful for directing expression of mycobacterial genes in E. coli. Further, this promoter sequence can also be used to express homologous and/or heterologous genes in a mycobacterium, thus providing a key element for the development of gene expression systems in mycobacteria.

In order to derive information about the possible biological function of the MBB51A protein, the amino acid sequence of this protein was used to search for homology against available sequences in the PIR Protein Database Release 20 (Table I) and a Genebank Nucleic Acid Database (Table II) using the FastA suite of programs written by (Lipman and Pearson, Proc. Natl. Acad. Sci., USA, 85:2 (1988)). The MBB51A protein sequence exhibited homology to a family of ion-motive ATPases from different organisms, ranging from bacteria to mammals. The 13 best scores from a search with ktuple 2 are shown in the upper panel of Table I and 10 best scores from a search with ktuple 1 are shown in the lower panel. In each case, MBB51A protein exhibited maximum homology (75.9% homology in a 593 amino acid overlap with 31.9% identity to a K+ transporting ATPase of S. faecalis (Solioz et al., 1987). The next best homology was observed with the B-chain of K+ transporting ATPase of E. coli (Hesse, et al., Proc. Natl. Acad. Sci., U.S.A., 81:4746–4750 (1984)) (68.8% homology in a 397 amino acid overlap with 24.2% identity). A lesser extent of homology was also seen with H+, Ca++ and Na+-ATPases from different organisms. The results of homology search thus indicated that MBB51A protein is an ion-motive ATPase of M. bovis BCG and is closely related to the other bacterial ion-motive ATPases. This is the first report of the cloning and identification of such an ATPase in mycobacteria. The BCG ion-motive ATPase showed homologies with other ion-motive ATPases with overlapping regions ranging in size from 593 amino acids in case of S. faecalis to 82 amino acids as in case of L. donovani, (Meade, et al., Mol. Cell Diol., 7, 3937–3946 (1987)), though most of the regions of sequence identity or conservation were localized in the C-terminal half of the MBB51A protein. Further, a region of 30 amino acids in the C-terminal half of MBB51A protein was found to be shared with most of these ATPases, thereby suggesting the functional importance of this region. Detailed alignment of MBB51A protein with the K+ ATPases of S. faecalis and E. coli also indicated that several residues were conserved between the three ATPases, including the ones that are invariant in all ATPases from bacteria to man.

TABLE I

RESULTS OF HOMOLOGY SEARCH OF MBB51A AMINO ACID SEQUENCE AGAINST PIR PROTEIN DATABASE

| LOCUS | SHORT DEFINITION | initn | opt |
|---|---|---|---|
| ktuple: 2 | | | |
| >A29576 | Potassium - transporting ATPase Streptococcus | 547 | 792 |
| >PWECBK | Potassium - transporting ATPase, β chain - E. coli | 314 | 270 |
| >A25939 | Proton - transporting ATPase - Neurospora | 168 | 186 |
| >A25823 | Proton - transporting ATPase - Yeast | 166 | 184 |
| >PWRBFC | Calcium - transporting ATPase, fast twitch skele | 152 | 158 |
| >PWRBSC | Calcium - transporting ATPase, slow twitch skele | 135 | 157 |
| >A25344 | Potassium - transporting ATPase - Rat | 78 | 155 |
| >RDEBHA | Mercuric reductase - Shigella flexneri plasmid | 99 | 142 |
| >RDPSHA | Mercuric reductase (transposon Tn501) | 74 | 124 |
| >RGPSHA | Mercuric resistance operon regulatory p | 79 | 109 |
| >A24639 | Sodium/potassium-transporting ATPase, alpha | 92 | 82 |
| >A24414 | Sodium/potassium-transporting ATPase, alpha | 92 | 82 |
| >B24862 | Sodium/potassium-transporting ATPase, beta | 83 | 82 |

The PIR protein data base (2378611 residues in 9124 sequences) was scanned with the FASTA program. The mean of the original initial score was 27.2 with a standard deviation of 6.9. Initial scores (initn) higher than 75.6 are 6 standard deviations above the average, a level of significance that usually indicates biological relatedness. Optimization (opt) generally will improve the initial score of related proteins by introducing gaps in the sequence. Unrelated sequences usually do not have their scores improved by optimization.

| LOCUS | SHORT DEFINITION | initn | opt |
|---|---|---|---|
| ktuple: 1 | | | |
| >A29576 | potassium-transporting ATPase - Streptococcus | 744 | 792 |
| >PWECBK | potassium-transporting ATPase, β chain - Esche | 386 | 270 |
| >A25939 | Proton-transporting ATPase - Neurospora crassa | 310 | 186 |
| >A25823 | proton-transporting ATPase - Yeast (Saccharomy) | 317 | 184 |
| >B24639 | Sodium/potassium-transporting ATPase, alpha (+ | 158 | 163 |
| >A24639 | Sodium/potassium-transporting ATPase, alpha ch | 175 | 160 |
| >C24639 | Sodium/potassium-transporting ATPase, alpha (II | 192 | 159 |
| >PWRBFC | Calcium-transporting ATPase, fast twitch skele | 240 | 158 |
| >PWSHNA | Sodium/potassium-transporting ATPase, alpha skele | 214 | 158 |
| >A24414 | Sodium/potassium-transporting ATPase, alpha chain | 214 | 158 |

TABLE II

RESULTS OF HOMOLOGY SEARCH OF MBB51A AMINO ACID SEQUENCE AGAINST GENBANK NUCLEIC ACID SEQUENCE DATABASE

| LOCUS | SHORT DEFINITION | initn | opt |
|---|---|---|---|
| ktuple: 2 | | | |
| >STRATPK | S. faecalis K+ ATPase, complete cds. | 537 | 800 |
| >ECOKDPABC | E. coli kdpABC operon coding for Kdp-ATPase | 314 | 270 |
| >YSPPMA1A | S. pombe H+ ATPase, complete cds. | 135 | 188 |
| >NEUATPASE | N. crassa plasma membrane ATPase, complete | 133 | 186 |
| >NEUATPPM | Neurospora crassa plasma membrane H+ ATPase | 131 | 186 |
| >YSCPMA1 | Yeast PMA1 for plasma membrane ATPase | 166 | 184 |
| >M17889 | FIG. 2. N of L. donovani ATPase and | 166 | 170 |
| >M12898 | Rabbit fast twitch skeletal muscle Ca++ ATPas | 140 | 158 |
| >RABATPAC | Rabbit Ca + Mg dependent Ca++ ATPase mRNA, co | 142 | 157 |
| >NR1MER | Plasmid NR1 mercury resistance (mer) operon. | 100 | 143 |
| ktuple: 1 | | | |
| >STRATPK | S. faecalis K+ ATPase gene, complete cds. | 744 | 800 |
| >SYNCATPSB | Cyanobacterium Synechococcus 6301 DNA for AT | 379 | 422 |
| >ECOKDPABC | E. coli kdpABC operon coding for Kdp-ATPase p | 379 | 270 |
| >YSPPMA1A | S. pombe H+ ATPase gene, complete cds. | 275 | 188 |
| >NEUATPASE | N. crassa plasma membrane ATPase gene, comple | 311 | 186 |
| >NEUATPPM | Neurospora crassa plasma membrane H+ ATPase | 302 | 186 |
| >YSCPMA1 | Yeast PMA1 gene for plasma membrane ATPase | 317 | 184 |
| >J04004 | Leishmania donovani, cation transporting ATP | 322 | 170 |
| >M17889 | FIG. 2. Nucleotide seguence of L. donovani | 306 | 170 |
| >RATATPA2 | Rat Na+,K+ ATPase alpha (+) isoform catalytic | 158 | 163 |

The KdpB protein of E. coli and possibly the S. faecalis K+ ATPase are members of E1E2-ATPases which are known to form an aspartyl phosphate intermediate, with cyclic transformation of the enzyme between phosphorylated and dephosphorylated species. By analogy to other ATPases, the phosphorylated Asp residue (D) (Furst, et al., J. Biol. Chem., 260:50–52 (1985)) was identified at position 443 in the MBB51A ATPase. This residue is the first of a pentapeptide sequence DKTGT that has been conserved in ATPases from bacteria to man, and must form an essential element of the catalytic site. Similarly, proline (P) at position 400 in MBB51A ATPase was found to be an invariant amino acid in other ATPases and is predicted to be located in a membrane spanning domain. Such membrane buried proline residues have been hypothesized to be required for the reversible conformational changes necessary for the regulation of a transport channel (Brandl, et al., Proc. Natl. Acad. Sci., U.S.A., 83:917–921 (1986)). In addition, other sequence motifs believed to be functionally important in other ion-motive ATPases were also found to be conserved in the MBB51A ATPase. These include a Gly (G) (Farley and Faller, J. Biol. Chem., 260:3899–3901 (1985)) at position 521 and Ala (A) (Ohta, et al., Proc. Natl. Acad. Sci., U.S.A., 83:2071–2075 (1986)) at position 646, and are shown in FIG. 5.

Since the MBB51A ATPase was homologous to membrane associated ATPases, characterization of the membrane associated helices in MBB51A protein was performed by computer algorithms. Using a hydropathy profile (Rao, et al., Biochem. Biophys. Acta., 869:197–214 (1986)), seven transmembrane domains in the MBB51A protein were identified and are shown in Table III and FIG. 5. Nearly the same transmembrane domains were also identified using the hydrophobic moment plot (Eisenberg et al., J. Mol. Biol., 179:125–142 (1984)) and are also shown in Table III and FIG. 5. The average size of a transmembrane domain is around 21 residues, because 21 residues coil into an α-helix approximately the thickness of the apolar position of a lipid bilayer (32 Å). This size of a transmembrane domain is, however, flexible within the range of a few amino acids, as determined by the functional properties of a given membrane-associated protein. The transmembrane domains identified in MBB51A protein, range in size from 20–37 residues. The first six transmembrane domains span the membrane only once, as indicated by both the hydropathy profile and the hydrophobic moment plot. The seventh transmembrane domain may traverse the membrane twice. These features along with the membrane buried proline (P) at position 400, are in accordance with the channel transport functions of ion-motive ATPases, involving a reversible change in the conformation of these proteins. Such transmembrane domains further define the intracellular and extracellular domains of this molecule. See FIG. 5.

TABLE III

Figure 5:
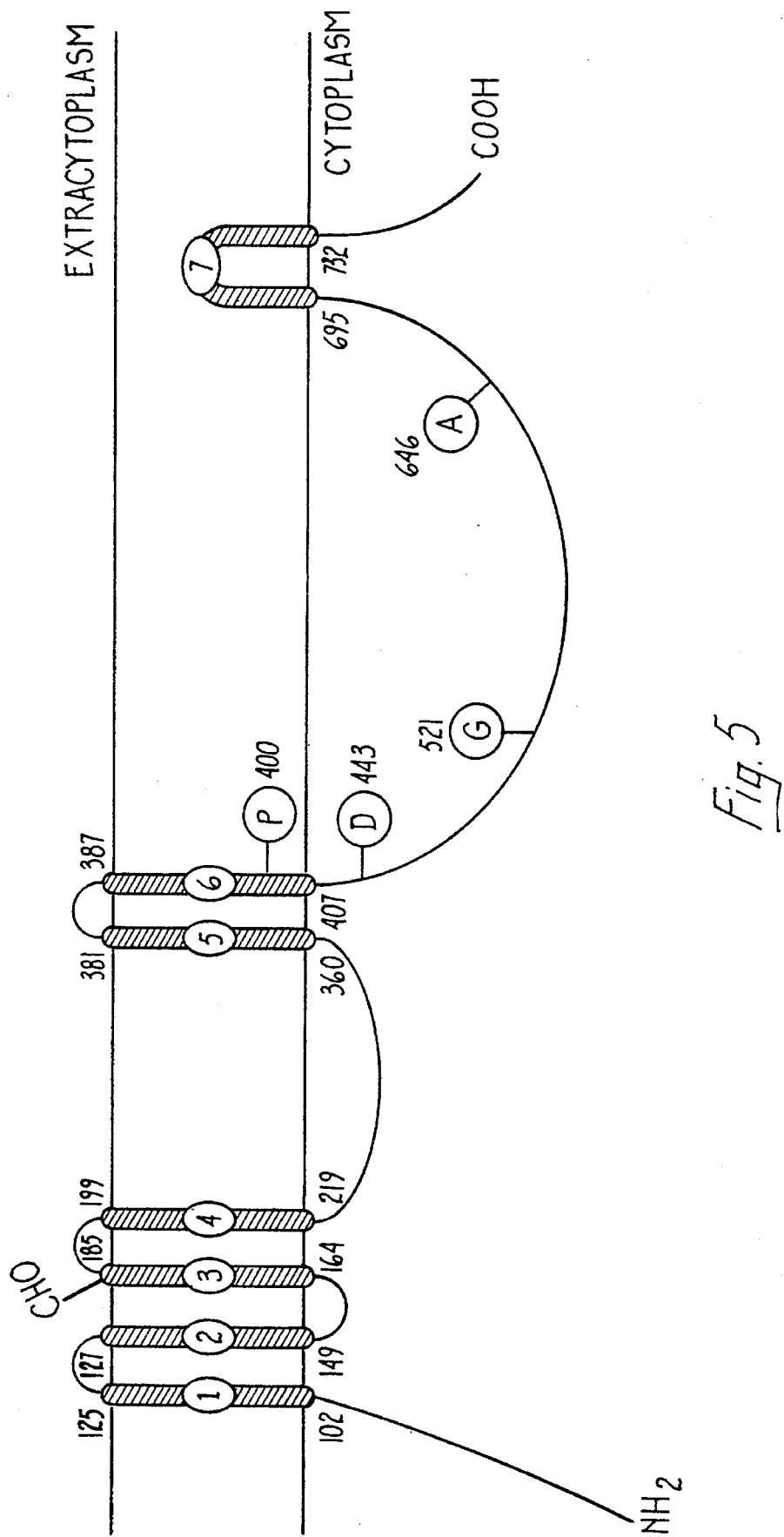

| Transmembrane Domain in FIG. 5 | Eisenberg Method | Rao & Argos Method |
|---|---|---|
| 1 | 102–122 | 98–125 |
| 2 | 129–149 | 127–147 |
| 3 | 164–184 | 164–185 |
| 4 | 199–219 | 198–220 |
| 5 | 361–381 | 360–382 |
| 6 | 387–407 | 387–419 |
| 7 | 703–723 | 695–732 |

The hydropathy profile of MBB51A protein was nearly superimposable over that of *S. faecalis* K+ ATPase, even though the MBB51A ATPase has at the N-terminus, 154 extra amino acids, which were absent in *S. faecalis*. This clearly puts in evidence the strong evolutionary conservation of the broad domain structure between these two proteins, making it more likely for the two proteins to have a similar three dimensional structural organization.

Based on the hydropathy profile and secondary structure predictions, a schematic model of the MBB51A ATPase is presented in FIG. 5. This model comprises at least seven transmembrane domains which span the membrane once are indicated along with the respective amino acid positions in FIG. 5. This model further defines extracellular and intracellular domains of the MBB51A protein. Many of the residues which have been shown to be functionally important in other ion-motive ATPases and are also conserved in the MBB51A protein, are also shown. Of these, proline (P) at position 400 is membrane-buried whereas as aspartic acid(D) at 443, glycine (G) at 521 and alanine (A) at 646, face the cytoplasm.

Figure 6B:
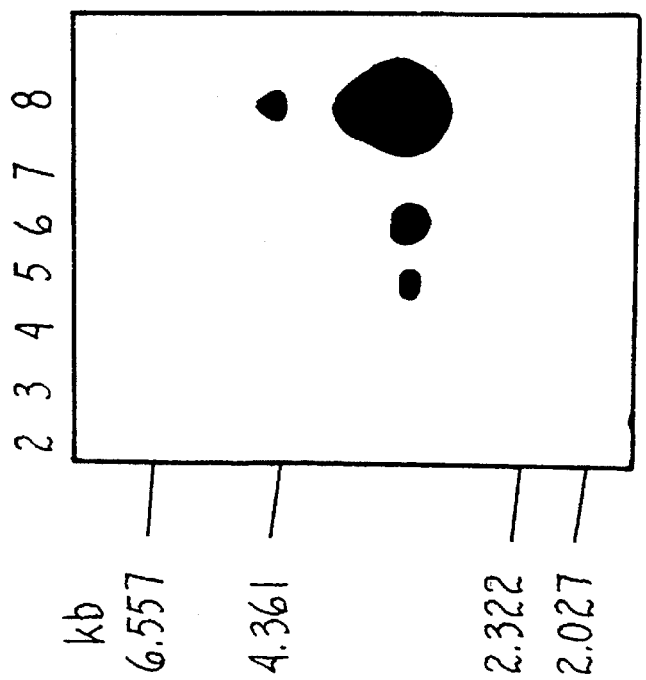
Figure 6A:
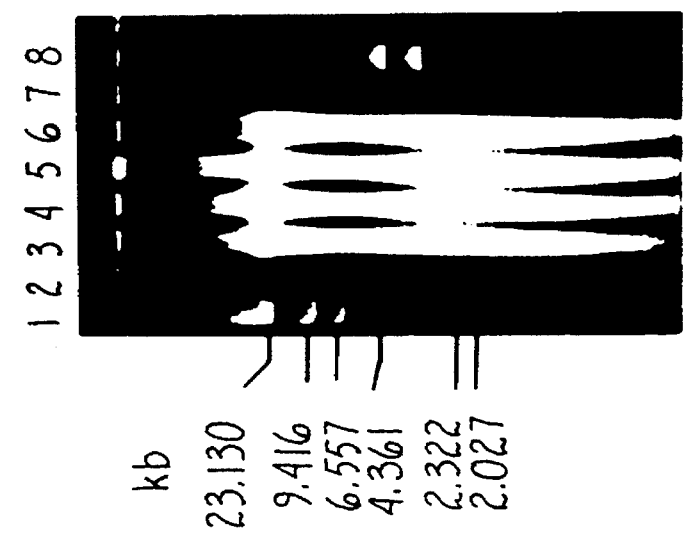

In order to determine whether the gene encoding MBB51A ion-motive ATPase is present in other mycobacterial strains related or unrelated to BCG, like the virulent strain *M. tuberculosis* H37Rv and other non-tuberculous, non-pathogenic mycobacteria like *M. vaccae* and *M. smegmatis*, Southern blot hybridization with genomic DNA from the above species was performed, using as probe BCG insert DNA from pMBB51A. As shown in FIG. 6, DNA hybridizable with the pMBB51A insert DNA was also present in *M. tuberculosis* H37Rv DNA but not in *M. smegmatis* and *M. vaccae*. This indicated that the *M. tuberculosis* H37Rv homologue of the pMBB51A gene has a similar genetic organization as seen in *M. bovis* BCG DNA, and is present on a 3.25 kb BamH I fragment.

The availability of novel *Mycobacterium bovis* BCG and/or *Mycobacterium tuberculosis* H37Rv antigens make it possible to address basic biochemical, immunological, diagnostic and therapeutic questions still unanswered about tuberculosis and *Mycobacterium tuberculosis*. For example, *Mycobacterium tuberculosis* specific antigenic determinants can be used to develop simple and specific seroepidemiological tests to screen human populations. Such serological tests are highly specific because of the use of antigenic determinants determined by the approaches described above and known to be unique to *Mycobacterium tuberculosis* H37Rv. Such serological tests are useful for early diagnosis of tuberculosis, thus permitting early treatment and limiting transmission of the disease from infected individuals to others.

Resistance to tuberculosis is provided by cell mediated immunity. The antigens identified here can be further used to determine which segments of these antigens are recognized by *Mycobacterium tuberculosis* specific T-cells. A mixture of peptides recognized by helper T-cells provides a specific skin test antigen for use in assessing the immunological status of patients and their contacts. A mixture of such peptides is also useful in evaluating rapidly the immunological efficacy of candidate vaccines. In addition peptides recognized by *Mycobacterium tuberculosis* specific T-cells can be components of a vaccine against the disease.

Knowledge of the complete nucleotide sequence of pMBB51A DNA insert provides a rich source of sequence information which can be used to design appropriate primers for PCR amplification of mycobacterial genomic DNA fragments. The ion-motive ATPase of BCG has areas of heavily conserved sequences (for, e.g., the ATP binding site) which are expected to be the same for all mycobacterial species and areas of sequence divergence (for, e.g., the N-terminal region) which are different in different mycobacterial species. Based on this knowledge primers can be designed either from the conserved regions or from the diverged regions to identify whether in a given sample the target DNA is mycobacterial versus non-mycobacterial, and in case of mycobacterial DNA, which mycobacterial species the DNA belongs.

Such amplification schemes are useful for the development of highly sensitive and specific PCR amplification based diagnostic procedures for mycobacteria. The observation that the 3.25 kb pMBB51A DNA insert is present in *Mycobacterium tuberculosis* H37Rv and *Mycobacterium bovis* BCG and is absent in avirulent *Mycobacterium vaccae* and *Mycobacterium smegmatis*, which have bearing on other aspects of the biological differences between these species, manifest in terms of virulence, growth characteristics and metabolism.

Recombinant vaccines can also be constructed by incorporating the DNA encoding all or part of the membrane-associated polypeptides of the invention into an appropriate vaccine vehicle. For example, all or part of the DNA encoding the 79 kD *Mycobacterium bovis* BCG protein or a portion of the protein can be incorporated into a vaccine vehicle capable of expressing the said DNA. Such a vaccine vehicle could be a virus for, e.g., vaccinia virus, etc., or a bacterium, e.g., mycobacteria, Salmonella, Vibrio, Bacillus, Yersinia, Bordetella, etc. to produce a vaccine capable of conferring long-lasting immunity on individuals to whom it is administered.

A special feature of the 79 kD BCG ion-motive ATPase is that it is a membrane bound antigen. Therefore, it can be used to link foreign DNA sequences encoding antigenic epitopes (B-cell epitopes or T-cell epitopes) of interest, with this gene or a portion of this gene in a manner which causes the foreign epitope to be used as an immunogen. Such linkages can be engineered into extracellular or intracellular domains of MBB51A protein, or into a combination of both types of domains. Engineering of immunogenic foreign epitopes into MBB51A DNA is accomplished by standard recombinant DNA methods known to those skilled in the art. Some of these methods involve use of unique restriction sites, in vitro mutagenesis and/or PCR-related methods. One such convenient method involves the use of a unique NdeI site at position 1090 in the MBB51A DNA where foreign DNA can be inserted. Grafting of epitopes on the cell surface induces rapid antibody response by virtue of the epitope being well-exposed on the bacterial cell, which in turn leads to direct activation of B cells. In addition, intracellular localization of an epitope induces B cell memory and a proficient T cell response. Examples of epitopes of interest known to be involved in the immune response to various pathogens include epitopes from *E. coli* LT toxin, foot and mouth disease virus, HIV, cholera toxin, etc.

Thus, the 79 kD antigen is useful in the design of recombinant vaccines against different pathogens. Such vaccines comprise a recombinant vaccine vehicle capable of expressing all or part of the 79 kD membrane-associated protein of mycobacteria, into which foreign epitopes have been engineered, such that the foreign epitopes are expressed on the outer surface and/or on the inner side of the cell membrane, thereby rendering the foreign epitopes immunogenic. The vaccine vehicle for this purpose may be a cultivable mycobacterium for, e.g., BCG. In these applications, the BCG ion-motive ATPase gene can be borne on a mycobacterial shuttle vector or alternately the foreign DNA encoding antigenic epitopes of the immunogenic polypeptides can be inserted into the mycobacterial genome via homologous recombination in the ion-motive ATPase gene or random integration. Such a process yields stable recombinant mycobacterial strains capable of expressing on their surface and/or in the cytoplasm antigenic sequences of interest, which can, for example, provide protection against a variety of infectious pathogens. Targeting of recombinant antigens to the cell-wall is attractive not only because of the high immunogenicity of mycobacterial cell-walls but, in addition, because of concerns with the introduction of a live vaccine in populations with a high prevalence of HIV seropositivity. Additionally, based on the MBB51A protein, a non-living but immunogenic recombinant cell surface subunit vaccine can also be developed to provide a useful alternative to live vaccines. Alternately, other bacterial, viral or protozoan vaccine vehicles could be transformed to generate such recombinant vaccines. Examples of potential vaccine vehicles include vaccinia virus, pox-viruses, Salmonella, Yerisinia, Vibrio, Bordetella, Bacillus, etc.

Further, using such an approach, multivalent recombinant vaccines which allow simultaneous expression of multiple protective epitopes/antigens of different pathogens, could also be designed.

Equivalents

Those skilled in the art will recognize, or be able to ascertain, using no more than routine experimentation, many equivalents to the specific materials and components described specifically herein. Such equivalents are intended to be encompassed in the scope of the following claims.

What is claimed is:

1. An isolated nucleic comprising the coding sequence shown in SEQ ID NO: 1.

2. An isolated nucleic acid comprising a sequence which encodes a *M. bovis* BCG protein having the sequence shown in SEQ ID NO: 2.

3. An isolated nucleic acid comprising a sequence which encodes a protein of a mycobacterium other than *M. bovis* BCG, wherein said protein is a homolog of the protein of claim 2;

is an immunogenic membrane-associated protein of said mycobacterium; and is encoded by DNA which will hybridize with a DNA probe having the complete sequence represented in SEQ ID NO: 1 where, on a Southern blot, said probe identifies single 3.25 kb BamHI fragments *M. bovis* BCG and *M. tuberculosis* H37 Rv DNA but does not hybridize with BamHI-digested DNA from either *M. smegmatis* or *M. vaccae*.

4. The isolated nucleic acid of claim 3 wherein said other mycobacterium is selected from the group consisting of *M. tuberculosis, M. leprae, M. africanum, M. microti, M. avium, M. intracellulare, M. scrofulaceum* and a species of *M. bovis* other than *M. bovis* BCG.

5. A replicable vector comprising a nucleic acid according to any one of claims 1–4.

6. A host cell transformed with a vector according to claim 5.

7. A method of expressing an immunogenic mycobacterial protein, comprising the step of culturing a suitable host cell according to claim 6 under conditions suitable for the expression of said nucleic acid in said host cell.

8. An isolated nucleic acid comprising a sequence encoding the second or third extracellular domain of the protein having the sequence shown in SEQ ID NO: 2.

9. An isolated nucleic acid comprising a sequence encoding an intracellular domain of the protein having the sequence shown in SEQ ID NO: 2.

10. An isolated nucleic acid comprising a sequence encoding a transmembrane domain of the protein having the sequence shown in SEQ ID NO: 2.

11. A replicable vector comprising a nucleic acid according to any one of claims 8–10.

12. A host cell transformed with a vector according to claim 11.

* * * * *